US008841268B2

(12) United States Patent
Suzuki et al.

(10) Patent No.: US 8,841,268 B2
(45) Date of Patent: Sep. 23, 2014

(54) METHOD AND KIT FOR DETECTION OF CANCER, AND THERAPEUTIC AGENT FOR CANCER

(75) Inventors: Hiromu Suzuki, Hokkaido (JP); Minoru Toyota, Hokkaido (JP); Kohzoh Imai, Hokkaido (JP); Yasuhisa Shinomura, Hokkaido (JP); Takashi Tokino, Hokkaido (JP)

(73) Assignee: Sapporo Medical University, Hokkaido (JP)

( * ) Notice: Subject to any disclaimer, the term of this patent is extended or adjusted under 35 U.S.C. 154(b) by 645 days.

(21) Appl. No.: 12/991,335

(22) PCT Filed: May 7, 2009

(86) PCT No.: PCT/JP2009/002007
§ 371 (c)(1),
(2), (4) Date: Feb. 9, 2011

(87) PCT Pub. No.: WO2009/136501
PCT Pub. Date: Nov. 12, 2009

(65) Prior Publication Data
US 2011/0130341 A1 Jun. 2, 2011

(30) Foreign Application Priority Data
May 7, 2008 (JP) .................................. 2008-121671

(51) Int. Cl.
| C12N 15/11 | (2006.01) |
| A61K 48/00 | (2006.01) |
| C12Q 1/68 | (2006.01) |
| C07H 21/02 | (2006.01) |

(52) U.S. Cl.
USPC ....... 514/44 A; 514/44 R; 435/6.11; 536/24.5

(58) Field of Classification Search
None
See application file for complete search history.

(56) References Cited

U.S. PATENT DOCUMENTS

| 6,805,869 B2 * | 10/2004 | Guo ............................ 424/278.1 |
| 8,399,248 B2 * | 3/2013 | Cleary et al. ................... 435/325 |
| 2007/0161004 A1 * | 7/2007 | Brown et al. ..................... 435/6 |
| 2010/0227909 A1 * | 9/2010 | Cleary et al. ................ 514/44 A |

FOREIGN PATENT DOCUMENTS

WO  WO 2008/137862  * 11/2008

OTHER PUBLICATIONS

Corney et al (Cancer Res 67(18): 8433-8438, 2007).*
Lujambio et al (PNAS 105(36): 13556-13561, Sep. 9, 2008).*
Toyota et al (Cancer Res 2008; 68: (11). Jun. 1, 2008).*

Auer, R.L. et al., "Identification of a Potential Role for POU2AFI and BTG4 in the Deletion of II q23 in Chronic Lymphocytic Leukemia," *Genes, Chromosomes and Cancer* 2005; 43:1-10.
Corney, D.C. et al., "*MicroRNA-34b* and *MicroRNA-34c* Are Targets of p53 and Cooperate in Control of Cell Proliferation and Adhesion-Independent Growth," *Cancer Research* 2007; 67(18):8433-8438.
Eads, C.A. et al., "Combined Bisulfite Restriction Analysis (COBRA)," *Methods in Molecular Biology*, 2002; 200:71-85.
Galm, O. et al., "Methylation-Specific Polymerase Chain Reaction," *Methods in Molecular Medicine* 2005; 113:279-291.
Grady, W.M. et al., "Epigenetic silencing of the intronic microRNA *hsa-miR-342* and its host gene *EVL* in colorectal cancer," *Oncogene* published online: Feb. 11, 2008; 27:3880-3888.
He, L. et al., "A microRNA polycistron as a potential human oncogene," *Nature* 2005; 435:828-833.
He, L. et al., "A microRNA component of the p53 tumour suppressor network," *Nature* 2007; 447:1130-1134.
Johnson, S.M. et al., "*RAS* Is Regulated by the *let-7* MicroRNA Family," *Cell* 2005; 120:635-647.
Lehmann, U. et al., "Epigenetic inactivation of microRNA gene *hsa-mir-9-1* in human breast cancer," *Journal of Pathology* published online: Oct. 18, 2007; 214:17-24.
Lu, J. et al., "MicroRNA expression profiles classify human cancers," *Nature* 2005; 435:834-838.
Lujambio, A. et al., "CpG Island Hypermethylation of Tumor Suppressor microRNAs in Human Cancer," *Cell Cycle* 2007; 6(12):1455-1459.
Lujambio, A. et al., "Genetic Unmasking of an Epigenetically Silenced microRNA in Human Cancer Cells," *Cancer Research* 2007; 67:1424-1429.
Lujambio, A. et al., "A microRNA DNA methylation signature for human cancer metastasis," *PNAS* 2008; 105(36):13556-13561.
O'Donnell, K.A. et al., "c-Myc-regulated microRNAs modulate E2F1 expression," *Nature* 2005; 435:839-843.
Rouault, J-P. et al., "Identification of *BTG2*, an antiproliferative p53-dependent component of the DNA damage cellular response pathway," *Nature Genetics* 1996; 14:482-486.

(Continued)

*Primary Examiner* — Richard Schnizer
(74) *Attorney, Agent, or Firm* — Wolf, Greenfield & Sacks, P.C.

(57) ABSTRACT

The object aims to comprehensively analyze miRNA that undergoes epigenetic silencing in cancer to identify miRNA associated with cancer, elucidate the role of the identified miRNA in cancer, and develop a novel method for detecting cancer and a novel therapeutic agent for cancer both of which relate to the miRNA. Disclosed is a method for detecting cancer in a subject, which comprises detecting methylated CpG in a CpG island located in a promoter region of a microRNA 34b gene and/or a microRNA 34c gene in a biological sample collected from the subject. Also disclosed is a therapeutic agent for cancer, which comprises a nucleic acid encoding a BTG4 gene or BTG4, or comprises a nucleic acid encoding a miR-34b gene and/or an miR-34c gene or miR-34b and/or miR-34c.

18 Claims, 20 Drawing Sheets

(56) References Cited

OTHER PUBLICATIONS

Thomson, J. M. et al., "Extensive post-transcriptional regulation of microRNAs and its implications for cancer," *Genes & Development* 2006; 20:2202-2207.

Tost, J. et al., "DNA methylation analysis by pyrosequencing," *Nature Protocols* 2007; 2(9):2265-2275.

Toyota, M. et al., "Epigenetic Silencing if *MicroRNA-34b/c* and *B-Cell Translocution Gene 4* is Associated with CpG Island Methylation in Colorectal Cancer," *Cancer Research* 2008; 68(11):4123-4132.

Trinh, B. N. et al., "DNA Methylation Analysis by MethyLight Technology," *Methods* 2001; 25:456-462.

Warnecke, P. M. et al., "Identification and resolution of artifacts in bisulfite sequencing," *Methods* 2002; 27:101-107.

Weber, B. et al., "Methylation of Human MicroRNA Genes in Normal and Neoplastic Cells," *Cell Cycle* 2007; 6(9):1001-1005.

[No Author Listed] Principles of cancer therapy. The Merck manual of diagnosis and therapy. 18$^{th}$ edition. 2006;1157-1171.

Buanne et al., Cloning of PC3B, a novel member of the PC3/BTG/TOB family of growth inhibitory genes, highly expressed in the olfactory epithelium. Genomics. Sep. 15, 2000;68(3):253-63.

Dong et al., Frequent promoter hypermethylation and transcriptional downregulation of BTG4 gene in gastric cancer. Biochem Biophys Res Commun. Sep. 11, 2009;387(1):132-8. doi: 10.1016/j.bbrc.2009.06.140. Epub Jul. 1, 2009.

Office Action for Japanese Application No. 2010-511025 mailed Nov. 26, 2013.

European Office Communication mailed Jul. 7, 2014 for application EP 09 742 626.6.

\* cited by examiner

Fig. 9C

Results of an analysis of methylation in colorectal cancer cases.

| | |
|---|---|
| methylation-positive | 114 (90%) |
| methylation-negative | 12 (10%) |
| total | 126 |

| level | number | mean | standard deviation | standard error | lower 95% | upper 95% |
|---|---|---|---|---|---|---|
| m | 15 | 33.7593 | 9.67661 | 1.9790 | 29.832 | 37.687 |
| n | 46 | 22.3098 | 6.35997 | 1.1301 | 20.067 | 24.553 |
| s | 39 | 21.3336 | 8.21928 | 1.2273 | 18.898 | 23.769 |

| level | number | mean | standard deviation | standard error of mean | lower 95% | upper 95% |
|---|---|---|---|---|---|---|
| m | 15 | 33.7593 | 9.67661 | 2.4985 | 28.401 | 39.118 |
| n | 46 | 22.3098 | 6.35997 | 0.9377 | 20.421 | 24.198 |
| s | 39 | 21.3336 | 8.21928 | 1.3161 | 18.669 | 23.998 |

| level | difference | standard error of difference | lower confidence limit | upper confidence limit | p value |
|---|---|---|---|---|---|
| m s | 12.42574 | 2.328654 | 6.88298 | 17.96850 | <.0001* |
| m n | 11.44955 | 2.278906 | 6.02520 | 16.87390 | <.0001* |
| n s | 0.97619 | 1.668339 | -2.99486 | 4.94724 | 0.8284 | m multiple cancer case
s single cancer case
n non-cancer case

| level | number | mean | standard error | lower 95% | upper 95% |
|---|---|---|---|---|---|
| adenoma | 12 | 22.8558 | 3.7220 | 15.274 | 30.437 |
| cancer | 18 | 41.9450 | 3.0390 | 35.755 | 48.135 |
| sev-m | 5 | 34.8080 | 5.7661 | 23.063 | 46.553 |

| level | | difference | standard error of difference | lower confidence limit | upper confidence limit | p-value |
|---|---|---|---|---|---|---|
| cancer | adenoma | 19.08917 | 4.805064 | 7.28134 | 30.89700 | 0.0011* |
| sev-m | adenoma | 11.95217 | 6.863004 | -4.91279 | 28.81712 | 0.2057 |
| cancer | sev-m | 7.13700 | 6.517906 | -8.87992 | 23.15392 | 0.5241 |

Adenoma to moderate adenoma
Cancer cancer at and deeper than sm
Sev-m severe atypical adenoma - intramucosal carcinoma

Fig. 19

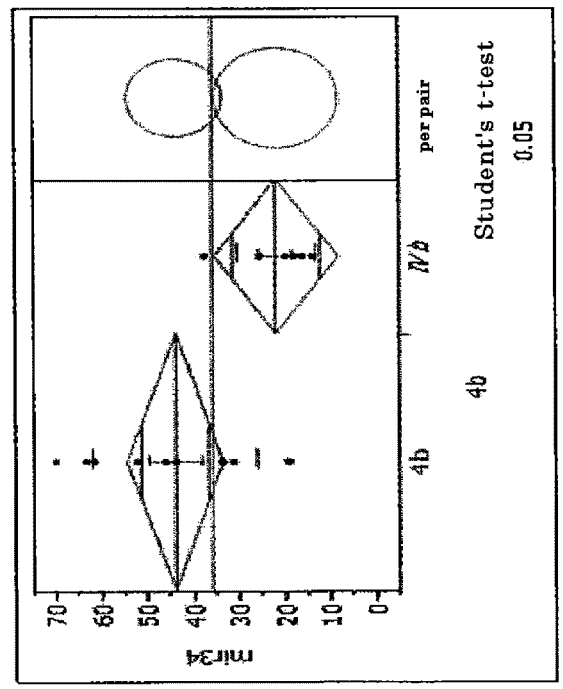

| level | number | mean | standard error | standard error of mean | lower 95% | upper 95% |
|---|---|---|---|---|---|---|
| 4b | 10 | 44.4810 | 18.0786 | 5.7170 | 31.548 | 57.414 |
| IVb | 6 | 22.4200 | 8.5443 | 3.4882 | 13.453 | 31.387 | unequal variance assumed

| | | | |
|---|---|---|---|
| difference | -22.061 | p-value | -3.29412 |
| standard error of difference | 6.697 | degree of freedom | 13.56449 |
| upper confidence limit of difference | -7.654 | p-value (Prob>|t|) | 0.0055* |
| lower confidence limit of difference | -36.468 | p-value (Prob>t) | 0.9972 |
| confidence level | 0.95 | p-value (Prob<t) | 0.0028* |

4b: cases with a type-V Pit within the same lesion
(e.g. associated with a severe atypism, intra-adenomatous carcinoma or cancer)

IVb: simple moderate adenoma

METHOD AND KIT FOR DETECTION OF CANCER, AND THERAPEUTIC AGENT FOR CANCER

RELATED APPLICATIONS

This application is a national stage filing under 35 U.S.C. §371 of international application PCT/JP2009/002007, filed May 7, 2009, the disclosure of which is incorporated by reference herein in its entirety.

FIELD OF THE INVENTION

The present invention is directed to methods of detecting cancer and kits for detecting cancer, as well as therapeutic agents for cancer.

BACKGROUND ARTS

MicroRNA (hereinbelow may be referred to as miRNA) is a short non-coding RNA of 21 to 22 bases. A precursor, primary miRNA, is processed by Drosha to produce a pre-miRNA, which is further processed by RISC complex comprising DICER to produce a mature miRNA. It then interferes with mRNA-to-protein translation of numerous target genes that are homologous to itself, suppressively controlling expression of various genes (FIG. 1).

Recently, since the involvement of miRNA in cancer was suggested, intensive studies focused on the relation between cancer and miRNA have been made, beginning to reveal the critical role of miRNA in cancer to control the expression of oncogenes and tumor suppressor genes. It has been shown that expression of many miRNAs is decreased in tumor tissue compared to in normal tissue (see, non-patent references 1 and 2). It is also reported that certain type of miRNA whose expression is decreased in tumor cell functions in a manner like a tumor suppressor gene by suppressing expression of oncogenes (see, non-patent reference 3). On the other hand, there has been reports suggesting, for those miRNAs that are overexpressed in tumor tissue, that oncogenes induce their expression, and that they function in an oncogene-like manner being involved in tumor formation (see, non-patent references 4 and 5).

Besides, studies have also been made to approach to the relation between miRNA and cancer from the aspect that miRNA functions as the target for tumor suppressor genes and oncogenes. For instance, an oncogene product Myc targets miR17-92, a miRNA cluster gene which is highly expressed in B cell lymphoma, and induces its expression (see, non-patent references 4 and 5). On the other hand, a tumor suppressor gene product p53 directly targets miRNA genes of miR-34 family consisting of miR-34a, miR-34b and miR-34c, and it has been shown that p53 is bound to p53-binding site located in the promoter region of miR-34a gene and miR-34b/c gene, thereby controlling the expression of each miRNA of miR-34 family (see, non-patent reference 6). Furthermore, each miRNA of miR-34 has been shown to have an effect of suppressing cell proliferation and inducing G1 arrest (see, non-patent references 6 and 7).

As described above, intensive studies have been made on the involvement of miRNA in cancer, and from their results it has been considered that miRNA analysis in cancer is important in order not only to elucidate the mechanism of carcinogenesis but also to obtain a basic knowledge for developing novel methods for diagnosis and treatment of cancer.

Meanwhile, inactivation of tumor suppressor gene is considered to be one factor of cancer development and/or progression, and a widely known mechanism of it is epigenetic suppression of gene expression (silencing). Particularly, cytosine methylation of a CpG (DNA methylation) in the region of transcription initiation of a gene is a phenomenon observed in almost any cancer. Many of the known tumor suppressor genes are reported to be silenced by DNA methylation. Recent discoveries of a series of genes that are specifically DNA-methylated in cancer imply that DNA methylation in cancer is as important as mutation and deletion as mechanism of genetic abnormalities associated with cancer development and/or progression. In the context of the aforementioned involvement of miRNA in cancer, studies have gradually been made on the relation between the silencing of miRNA by methylation and cancer (see, non-patent references 8 and 9).

Nevertheless, although there are hundreds of miRNAs, only a few among them have been implicated in specific cancer for their DNA methylation, and, many miRNAs are not even described for the specific function of their own. Therefore, most of miRNAs are yet to be analyzed in detail about their involvement in the epigenetic control of gene expression in cancer, and a large part thereof is still unclear.

[Non-patent reference 1] Lu J. et al., Nature, 435: 834-838, 2005

[Non-patent reference 2] Thomson J. M. et al., Genes & Development, 20: 2202-2207, 2006

[Non-patent reference 3] Johnson S. M. et al., Cell, 120: 635-647, 2005

[Non-patent reference 4] He L. et al., Nature, 435: 823-833, 2005

[Non-patent reference 5] O'Donnell K. A. et al., Nature, 435: 839-843, 2005

[Non-patent reference 6] He L. et al., Nature, 447: 1130-1134, 2007

[Non-patent reference 7] Corney D. C. et al., Cancer Research, 67: 8433-8438, 2007

[Non-patent reference 8] Lujambio A. et al., Cancer Research, 67: 1424-1429, 2007

[Non-patent reference 9] Lujambio A. et al., Cell Cycle, 15: 1455-1459, 2007

DISCLOSURE OF THE INVENTION

Problems to be Solved by the Invention

Accordingly, the object of the present invention is to identify a miRNA that is related to cancer, to elucidate its role in cancer, and to provide a novel method of detecting cancer and a therapeutic agent for cancer associated with said miRNA, by performing a global analysis of miRNAs that undergo epigenetic silencing in cancer.

Means to Solve the Problem

The inventors therefore made an intensive investigation to achieve the object above, and identified for the first time miR-34b and miR-34c as miRNAs whose expression are decreased under the control by epigenetic gene silencing in tumor cell-specific manner, and discovered that DNA methylation of CpG island in the promoter region of their genes is scarcely observed in normal tissue, but is at high level in tumor tissue. From these findings, the inventors discovered that the detection of cancer in a subject is enabled by detecting methylated CpG in the CpG island in the promoter regions of miR-34b gene and/or miR-34c gene in a biological sample obtained from the subject, thereby completed the invention.

The inventors further carried on the investigation based on these findings, and thus discovered that miR-34b and miR-34c target oncogenes, cell-cycle regulatory genes, etc., and suppress their expression. The inventors further discovered that the CpG island in the promoter region of miR-34b gene and/or miR-34c gene also functions as the promoter for BTG4 gene, which is transcribed in opposite direction to miR-34b and miR-34c, and discovered for the first time that the expression of BTG4 gene is decreased by epigenetic silencing in cancer cell, and that its gene product BTG4 has an ability of suppressing cell proliferation, thereby completed the cancer therapeutic agent of the invention.

Thus, the present invention is directed to a method of detecting a cancer in a subject, the method comprising:

detecting a methylated CpG in a CpG island in a promoter region of microRNA34b gene and/or microRNA34c gene in a biological sample obtained from the subject.

The present invention is also directed to said method wherein the cancer is detected according to a criteria that the methylated CpG in CpG island in the promoter region of microRNA34b and/or microRNA34c gene in the biological sample obtained from the subject are at least more than 10% of all CpGs in the CpG island in the promoter region of microRNA34b gene and/or microRNA34c gene in said biological sample obtained from the subject.

The present invention is further directed to said method wherein the CpG island in the promoter region of microRNA34b gene and/or microRNA34c gene is a DNA region having a nucleotide sequence that is identical to or substantially identical to the nucleotide sequence of SEQ ID NO:5.

The present invention is also directed to said method wherein the cancer is colorectal cancer, gastric cancer, pancreatic cancer or breast cancer.

Further, the present invention is also directed to said method wherein the biological sample is one or more selected from a group consisting of serum, stool, colon tissue, gastric lavage fluid, pancreatic juice and bile.

The invention is also directed to said method wherein the methylated CpG is detected using one or more procedures selected from the group consisting of methylation-specific PCR, bisulfite sequencing, pyro-sequencing, COBRA, and MethyLight.

Furthermore, the present invention is directed to said method wherein the methylated CpG is detected using a sense primer comprising successive 15 to 40 nucleotides of a nucleotide sequence that is identical to or substantially identical to the nucleotide sequence of SEQ ID NO:5, and an antisense primer comprising successive 15 to 40 nucleotides of a nucleotide sequence that is complementary to a nucleotide sequence that is identical to or substantially identical to the nucleotide sequence of SEQ ID NO:5.

The present invention is further directed to said method wherein the methylated CpG is detected using an oligonucleotide having a nucleotide sequence of any one of SEQ ID NOs:10, 11, 13, 14, 15, 17, 18, 19 and 20.

Moreover, the present invention is directed to a kit for cancer detection comprising a sense primer comprising successive 15 to 40 nucleotides of a nucleotide sequence that is identical to or substantially identical to the nucleotide sequence of SEQ ID NO:5, and an antisense primer comprising successive 15 to 40 nucleotides of a nucleotide sequence that is complementary to a nucleotide sequence that is identical to or substantially identical to the nucleotide sequence of SEQ ID NO:5.

The present invention is also directed to a kit for cancer detection comprising an oligonucleotide having a nucleotide sequence of any one of SEQ ID NOs:10, 11, 13, 14, 15, 17, 18, 19 and 20.

The present invention is further directed to a kit for cancer detection for detecting a cancer by any one of foregoing methods, the kit comprising a sense primer comprising successive 15 to 40 nucleotides of a nucleotide sequence that is identical to or substantially identical to the nucleotide sequence of SEQ ID NO:5, and an antisense primer comprising successive 15 to 40 nucleotides of a nucleotide sequence that is complementary to a nucleotide sequence that is identical to or substantially identical to the nucleotide sequence of SEQ ID NO:5.

Furthermore, the present invention is directed to a kit for cancer detection for detecting a cancer by any one of foregoing methods, the kit comprising an oligonucleotide having a nucleotide sequence of any one of SEQ ID NOs:10, 11, 13, 14, 15, 17, 18, 19 and 20.

The invention is also directed to a cancer therapeutic agent comprising a nucleic acid encoding BTG4 gene.

The invention is further directed to said cancer therapeutic agent wherein the nucleic acid encoding BTG4 gene is a nucleic acid encoding a protein having an amino acid sequence that is identical to or substantially identical to an amino acid sequence of SEQ ID NO:21.

Furthermore, the present invention is directed to a cancer therapeutic agent comprising BTG4.

The present invention is also directed to said cancer therapeutic agent wherein BTG4 is a protein having an amino acid sequence that is identical to or substantially identical to an amino acid sequence of SEQ ID NO:21.

Moreover, the present invention is directed to a cancer therapeutic agent comprising a nucleic acid encoding microRNA34b gene and/or microRNA34c gene.

The present invention is also directed to said cancer therapeutic agent wherein the nucleic acid encoding microRNA34b gene is encoding a polynucleotide sequence that is identical to or substantially identical to a polynucleotide sequence of SEQ ID NO:1, and the nucleic acid encoding microRNA34c gene is encoding a polynucleotide sequence that is identical to or substantially identical to a polynucleotide sequence of SEQ ID NO:3.

The present invention is further directed to a cancer therapeutic agent comprising microRNA34b and/or microRNA34c.

Furthermore, the present invention is directed to said cancer therapeutic agent wherein microRNA34b has a polynucleotide sequence that is identical to or substantially identical to a polynucleotide sequence of SEQ ID NO:2, and microRNA34c has a polynucleotide sequence that is identical to or substantially identical to a polynucleotide sequence of SEQ ID NO:4.

The Effects Exhibited by the Invention

The method of detecting cancer according to the present invention is based on the detection of a methylated CpG in a CpG island in a promoter region of miR-34b and/or miR-34c gene in a biological sample obtained from a subject. While the expression of miR-34b and/or miR-34c gene is kept high in normal tissue, it is decreased in tumor tissue-specific manner. The present invention, which detects the methylated CpG in the CpG island in the promoter region that directly control the expression of miR-34b and miR-34c, therefore permit an extremely accurate detection of cancer. Furthermore, the biological sample used for detection can be a tissue or tumor tissue obtained from the subject, such as colon tissue or colorectal tumor tissue, gastric tissue or gastric tumor tissue, as well as serum, stool, gastric lavage fluid, pancreatic juice and bile, which are relatively readily available and thereby facilitates cancer detection using the method of the present invention. Furthermore, the method according to the present invention can be carried out using methods such as methylation-specific PCR, bisulfite sequencing, pyro-sequencing, COBRA, MethyLight, and thus able to generate a detection result with high accuracy at high detection sensitivity in short time using extremely small amount of biological sample, thereby decreasing the subject's burden, and also contributes to early finding of cancer, predicting the stage of cancer, predicting a risk of recurrence of cancer, predicting a risk of carcinogenesis.

Also, similarly, the kit for cancer detection according to the present invention permits an easy detection of cancer with favorable accuracy, based on the fact that the target of detection, i.e., a methylated CpG in a CpG island in a promoter region of miR-34b and/or miR-34c gene, is specifically increased in tumor tissue but scarcely observed in normal tissue, and it is suitable for detecting cancer at extremely early stages, for monitoring recurrence of cancer, for detecting a risk of carcinogenesis, and for predicting the stage of cancer. In addition, the method and kit of the present invention are also useful in combination with other examination methods such as endoscopy, the combination would permit obtaining even more accurate examination result.

Furthermore, the therapeutic agent of the present invention comprises BTG4 or a nucleic acid encoding BTG4 gene, or miR-34b and/or miR-34c or a nucleic acid encoding miR-34b gene and/or miR-34c gene. The therapeutic agent of the present invention therefore is capable of suppressing proliferation of cancer cells through introducing BTG4 or miR-34b and/or miR-34c into a cancer cell, or expressing BTG4 gene or miR-34b and/or miR-34c gene in a cancer cell, providing an outstanding therapeutic effect. Furthermore, the expression of BTG4 or BTG4 gene, or miR-34b and/or miR-34c or miR-34b gene and/or miR-34c gene contained in the therapeutic agent of the present invention is being suppressed in tumor tissue while they are highly expressed in normal tissue. The therapeutic agent of the present invention therefore permits the tumor cell-specific recovery of the expression of gene or gene product that are being deactivated due to epigenetic abnormalities, while it causes no toxic effects on normal tissue, but exhibiting specific effect in target tumor tissue in needs of the treatment, with little side effect and high safety. It also serves for developing more effective therapy with less side effect.

THE BEST MODE FOR PERFORMING THE PRESENT INVENTION

The present invention is described in detail hereinbelow.

Unless otherwise stated herein, scientific and technical terms used in the context of the present invention have the meanings that are normally understood by a person with ordinary skill in the art. In general, terms and techniques used in the context of cell and tissue culture, molecular biology, immunology, microbiology, genetics and protein and nucleic chemistry are well known and normally used in the art. Also, unless otherwise stated, the methods and techniques of the present invention are carried out according to routine procedures that are well known in the art, as described in various general and more specialized references cited and discussed herein. Such references include, for example, Sambrook et al., Molecular Cloning: A Laboratory Manual, 2nd ed., Cold Spring Harbor Laboratory Press (1989) and Sambrook et al., Molecular Cloning: A Laboratory Manual, 3rd ed., Cold Spring Harbor Press (2001); Ausubel et al., Current Protocols in Molecular Biology, Greene Publishing Associates (1992, and supplementary of 2000); Ausubel et al., Short Protocols in Molecular Biology: A Compendium of Methods from Current Protocols in Molecular Biology—$4^{th}$ Ed., Wiley & Sons (1999); Harlow and Lane, Antibodies: A Laboratory Manual, Cold Spring Harbor Laboratory Press (1990); and Harlow and Lane, Using Antibodies: A Laboratory Manual, Cold Spring Harbor Laboratory Press (1999).

The terms as well as experimental procedures and techniques described herein in the context of analytical chemistry, synthetic organic chemistry, and pharmaceutical chemistry and medicinal chemistry are well known and normally used in the art. Standard techniques are used in chemical synthesis, chemical analysis, production, formulation and delivery of an agent, and treatment of a subject.

The term "subject" in the present invention means any individual of an organism, preferably a vertebrate, more preferably a mammal, still more preferably a human individual. In the present invention, the subject may be healthy or having some diseases, although where treatment for cancer is contemplated, a subject, e.g., a rodent such as mouse, rat, gerbil, guinea pig; a Felidae animal such as cat, puma, tiger; a Cervidae animal such as deer and elk; and a rabbit, dog, mink, sheep, goat, bovine, equine, monkey, human, etc., having or being experimentally made to have the disease is preferred.

Herein, unless otherwise stated, name of a protein is described in alphabets (or alphabets and digits), a gene encoding the protein is described by adding "gene" after said description in alphabets (or alphabets and digits) or by underlining said description in alphabets (or alphabets and digits). Therefore, unless otherwise stated, a simple description of "BTG4", for instance, means the protein itself of BTG4 (B cell translocation gene 4), whereas the description of "BTG4 gene" or "BTG4" (underlined) means a gene that encodes BTG4.

Also, with respect to the description of a microRNA (miRNA), when the miRNA itself is meant, its name is described, whereas when a DNA encoding it is meant, "gene" is added after the name, or the name is underlined. Therefore, unless otherwise stated, by "microRNA34b" or "miR-34b", miRNA itself of microRNA34b is meant, whereas by "microRNA34b gene" or "miR-34b gene" a DNA that encodes miRNA34b is meant, and by "miRNA-34b" (underlined), a DNA that encodes miRNA34b is meant too.

In the present invention, a method of detecting cancer in a subject is provided, the method comprising:

detecting a methylated CpG in a CpG island in a promoter region of miR-34b gene and/or miR-34c gene in a biological sample obtained from the subject.

As used herein, microRNA34b (also as described as miRNA-34b herein) and microRNA34c (also as described as miRNA-34c herein) are miRNAs derived from single precursor RNA transcribed from chromosome 11q23.1 in human. Examples of miRNA-34b include those encoded by a DNA sequence that is identical to or substantially identical to a DNA sequence of SEQ ID NO:1 (precursor miRNA-34b), and a matured type of miRNA-34b includes those having an RNA nucleotide sequence that is identical to or substantially identical to a nucleotide sequence of:

```
UAGGCAGUGUCAUUAGCUGAUUG      (SEQ ID NO: 2)
(miRNA accession number MI0000742).
```

Examples of miRNA-34c include those encoded by a DNA sequence that is identical to or substantially identical to a DNA sequence of SEQ ID NO:3 (precursor miRNA-34c), and a matured type of miRNA-34c includes those having an RNA sequence that is identical to or substantially identical to a nucleotide sequence of:

```
AGGCAGUGUAGUUAGCUGAUUGC      (SEQ ID NO: 4)
(miRNA accession number MI0000743).
```

Here, a DNA sequence that is substantially identical to a DNA sequence of SEQ ID NO:1 or 3 can be, for example, a nucleotide sequence having a homology of about 70% or more, preferably about 80% or more, more preferably about 90% or more, still more preferably about 95% or more, most preferably about 98% and more to a DNA nucleotide sequence of SEQ ID NO:1 or 3. Furthermore, in the present invention, as precursor miRNA-34b that are encompassed by miRNA-34b and encoded by the DNA sequence that is substantially identical to the DNA sequence of SEQ ID NO:1, preferably used are those which maintain the functions of the miRNA encoded by the nucleotide sequence of SEQ ID NO:1 at substantially equal level. Similarly, in the present invention, as precursor miRNA-34c that are encompassed by miRNA-34c and encoded by a DNA sequence that is substantially identical to the DNA sequence of SEQ ID NO:3, preferably used are those which maintain the functions of the miRNA encoded by the nucleotide sequence of SEQ ID NO:3 at substantially equal level.

Also, similarly, a nucleotide sequence that is substantially identical to the DNA sequence of SEQ ID NO:2 or 4 can be, for example, a nucleotide sequence having a homology of about 70% or more, preferably about 80% or more, more preferably about 90% or more, still more preferably about 95% or more, most preferably about 98% and more to the DNA sequence of SEQ ID NO:2 or 4. Furthermore, in the present invention, as those encompassed by miRNA-34b and have an RNA nucleotide sequence that is substantially identical to the nucleotide sequence of SEQ ID NO:2, preferably used are those which maintain the functions of a miRNA consisting of the nucleotide sequence of SEQ ID NO:2, i.e., for example, the suppressor function to the expression of oncogenes such as MET gene and MYB gene, at substantially equal level. Similarly, in the present invention, as those encompassed by miRNA-34c and have an RNA nucleotide sequence that is substantially identical to the nucleotide sequence of SEQ ID NO:4, preferably used are those which maintain the functions of a miRNA consisting of the nucleotide sequence of SEQ ID NO:4, i.e., for example, the suppressor function to the expression of oncogenes such as MET gene and MYB gene, at substantially equal level.

Furthermore, an miR-34b gene used in the present invention includes, for example, a DNA comprising a nucleotide sequence of SEQ ID NO:1, or a DNA comprising a nucleotide sequence that specifically hybridizes to the nucleotide sequence of SEQ ID NO:1 under a stringent condition and encoding a miRNA having substantially equal properties to a miRNA comprising the nucleotide sequence of SEQ ID NO:2. Here, as a DNA comprising a nucleotide sequence that specifically hybridizes to the nucleotide sequence of SEQ ID NO:1 under a stringent condition, a DNA comprising a nucleotide sequence having homology of about 60% or more, preferably about 70% or more, more preferably about 80% or more, still more preferably about 90% or more, particularly preferably about 95% or more, most preferably about 98% or more, to a nucleotide sequence that is complementary to the nucleotide sequence of SEQ ID NO:1 may be used.

Similarly, an miR-34c gene used in the present invention includes, for example, a DNA comprising a nucleotide sequence of SEQ ID NO:3, or a DNA comprising a nucleotide sequence that specifically hybridizes to the nucleotide sequence of SEQ ID NO:3 under a stringent condition and encoding a miRNA having substantially equal properties to the miRNA comprising the nucleotide sequence of SEQ ID NO:4. Here, as a DNA comprising a nucleotide sequence that specifically hybridizes to the nucleotide sequence of SEQ ID NO:3 under a stringent conditions, for example, a DNA comprising a nucleotide sequence having homology of about 60% or more, preferably about 70% or more, more preferably about 80% or more, still more preferably about 90% or more, particularly preferably about 95% or more, most preferably about 98% or more, to a nucleotide sequence that is complementary to the nucleotide sequence of SEQ ID NO:3 may be used.

A "stringent condition" herein are normally a condition of 42 degree Centigrade, 2×SSC and 0.1% SDS, preferably a condition of 65 degree Centigrade, 0.1×SSC and 0.1% SDS.

Although the nucleotide sequence of miR-34b gene and/or miR-34c gene may differ not only between different species but also even within the same species, due to polymorphism, isoforms, etc., a gene having different nucleotide sequence is still encompassed by miR-34b gene or miR-34c gene as long as it encodes miR-34b or miR-34c.

In the present invention, the promoter region of miR-34b and/or miR-34c gene is meant to refer to the region of 1000 bps in full length, from the 5' end of miR-34b gene to its 1000 bps upstream on chromosome, for example, in human, the region from the 5' end of miR-34b gene to 867 bps upstream thereof, particularly preferably the region from the 5' end of miR-34b gene to 756 bps upstream thereof.

In the present invention, a CpG island is a DNA region rich in CpGs (i.e., where a cytosine is on 5' side and a guanine is on 3' side, being adjacent and bound to each other by phosphodiester bond), wherein the CG content is 50% or more, and the ratio of existing CpG is 60% or more of the expected amount.

A CpG island in a promoter region of miR-34b and/or miR-34c gene can be used for the detection of cancer according to method of the present invention without limitation as long as it corresponds to the CpG island in the promoter region as described above, and includes, for example, in the case of human, a region of 987 bps in full length, from 748 bps upstream of the 5' end of miR-34b gene to 230 bps downstream of the 5' end of miR-34b gene. An exemplary nucleotide sequence includes those of SEQ ID NO:5 or having substantially identical nucleotide sequence thereto.

Among the CpG islands in the promoter region of human miR-34b and/or miR-34c gene described above, a region of 262 bps in full length from 111th to 372th nucleotide, for example, is preferred in the method of cancer detection according to the present invention. An example includes a region of 262 bps in full length from 111th to 372th nucleotide of the nucleotide sequence of SEQ ID NO:5 (the region consisting of the nucleotide sequence of SEQ ID NO:6) or a region having a nucleotide sequence that is substantially identical to it. More preferred is a region of 223 bps in full length from 144th to 366th nucleotide, and an example includes a region of 223 bps in full length from 144th to 366th nucleotide of the nucleotide sequence of SEQ ID NO:5 (the region consisting of the nucleotide sequence of SEQ ID NO:7) or a region having a nucleotide sequence that is substantially identical to it. Most preferred is a region of 134 bps in full length from 214th to 347th nucleotide, and an example includes a region of 134 bps in full length from 214th to 347th nucleotide of the nucleotide sequence of SEQ ID NO:5 (the region consisting of the nucleotide sequence of SEQ ID NO:8) or a region having a nucleotide sequence that is substantially identical to it.

Here, a nucleotide sequence that is substantially identical to a nucleotide sequence of SEQ ID NO:5, 6, 7 or 8 may include, for example, a nucleotide sequence having homology of about 70% or more, preferably about 80% or more, more preferably about 90% or more, still more preferably about 95% or more, most preferably about 98% or more, to the nucleotide sequence of SEQ ID NO:5, 6, 7 or 8.

Furthermore, the inventors have discovered that the promoter region of miR-34b gene and/or miR-34c gene overlaps the promoter region of BTG4 (B cell translocation gene 4) gene which is encoded in opposite direction (antisense direction) to miR-34b gene and/or miR-34c gene on the same chromosome (FIGS. 3B, 7 and 8A), and that the CpG island located on the promoter region of miR-34b gene and/or miR-34c gene has a promoter effect not only on miR-34b gene and/or miR-34c gene but also on BTG4 gene (FIGS. 8A and B).

Accordingly, the method, provided by the present invention, of detecting cancer in a subject comprising:

detecting a methylated CpG in a CpG island in a promoter region of miR-34b gene and/or miR-34c gene in a biological sample obtained from the subject can namely be described in other words as a method of detecting cancer in a subject comprising:

detecting a methylated CpG in a CpG island in a promoter region of BTG4 gene in a biological sample obtained from the subject.

In the method of the present invention, "detecting a methylated CpG" means detecting methylated cytosine in a DNA nucleotide sequence (i.e., DNA methylation).

The method of the invention may, as long as the method "comprises detecting a methylated CpG in a CpG island in a promoter region of microRNA34b and/or microRNA34c gene in a biological sample obtained from the subject", be carried out without any limitation in terms of the measure by which it is determined that cancer is present in the subject, and employ any criteria for detecting cancer that is appropriately selected according to individual situation and types of cancer. Nevertheless, because the ratio of methylated CpGs in a CpG island is low in normal tissue and high in tumor tissue, it is preferred to determine that cancer is present in the subject based on the criteria that the methylated CpGs in the CpG island in the biological sample obtained from the subject are quantitatively greater compared to the methylated CpGs in the CpG island in a biological sample obtained from a healthy subject from the same species as said subject, or compared to the methylated CpGs in the CpG island in a biological sample of the control normal tissue obtained from the same individual as said subject.

Moreover, according to the study by the inventors, it is discovered that the methylated CpGs in a CpG island in a promoter region of miR-34b gene and/or miR-34c gene share no more than 5 to 6% of total CpGs in the sample when the biological sample obtained from the subject is a normal tissue, whereas they are well over this when the biological sample obtained from the subject is a tumor tissue, being often more than 50%. However, when a biopsy specimen is used as the biological sample, which often contains an admixture of tumor and normal tissue, the high value of the tumor part is averaged with the low value of the normal tissue part, and the ratio of methylated CpGs in total CpGs in the sample tends to be expressed low even when cancer is actually present. Accordingly, in more suitable embodiments, the method of the present invention may detect cancer and determine the presence of cancer according to the criteria that the methylated CpGs in the CpG island in the promoter region of miR-34b and/or miR-34c gene in the biological sample obtained from the subject is at least more than 8%, preferably at least 10%, more preferably at least 20%, still more preferably at least 30% of total CpGs in the CpG island in said region in said biological sample obtained from the subject (i.e., total alleles in said sample).

In the method of the present invention, the detection of methylated CpGs may be carried out by any means without limitation, although it is preferred to use a known method for detecting DNA methylation (a methylated cytosine) such as methylation-specific PCR, bisulfite sequencing, pyro-sequencing, COBRA, and MethyLight, and any one of those methods may be used alone or in combination of two or more. Among foregoing methods, MethyLight is particularly preferably used for its ability of detecting methylation from a small amount of specimen with high sensitivity. Pyro-sequencing is also particularly preferably used when quantitative detection of methylation is aimed.

Methylation-specific PCR utilizes the difference in sensitivity to the cytosine-to-uracil conversion in the presence or absence of methylation, generating primers specific to methylated allele and unmethylated allele, amplifying and detecting them by PCR for detection. The obtained PCR product is subjected to electrophoresis on an agarose gel, stained with ethidium bromide, then the presence of methylation is determined by the presence of bands (see, Methods Mol Med. 2005; 113: 279-91, and Suzuki, H., Toyota, M. and K. Imai, "Bisulfite PCR: Shin Idenshi Kogaku Handbook", 4th edition, Muramatsu, M. and T. Yamamoto eds., Yodo-sha, pp 99-106, 2003).

Bisulfite sequencing utilizes bisulfite-treated DNAs to amplifies methylated and unmethylated alleles at the same time, and obtained PCR products are cloned into e.g., TOPO-cloning vector (Invitrogen), and then the presence or absence of methylation is detected by sequencing. It has an advantage that the methylation of all CpG sequences within the amplified region can be determined, although it may not be suitable for manifold analysis due to its requirement for heavy work for analysis (see, Methods. 2002 June; 27(2): 101-7, and Suzuki, H., Toyota, M. and K. Imai, "Bisulfite PCR: Shin Idenshi Kogaku Handbook", 4th edition, Muramatsu, M. and T. Yamamoto eds., Yodo-sha, pp 99-106, 2003).

Pyro-sequencing uses bisulfite-treated DNAs to amplify methylated and unmethylated alleles at the same time, then analyzes obtained PCR products by pyro-sequencing. The ratio of methylation is detected as the polymorphism of cytosine and thymine, calculated as [fluorescent intensity of cytosine/the sum of fluorescent intensities of cytosine and thymine]. It is useful as a quantitative and high-throughput methylation analysis (see, Nat Protoc. 2007; 2(9):2265-75).

COBRA method uses bisulfite-treated DNAs to amplify methylated and unmethylated alleles at the same time, and obtained PCR products are digested with restricted enzymes, then subjected to electrophoresis on an agarose gel, stained with ethidium bromide, and the presence or absence of methylation is determined according to the presence or absence of the bands cleaved by restriction enzymes (see, Methods Mol Biol. 2002; 200:71-85, and Suzuki, H., Toyota, M. and K. Imai, "Bisulfite PCR: Shin Idenshi Kogaku Handbook", 4th edition, Muramatsu, M. and T. Yamamoto eds., Yodo-sha, pp 99-106, 2003).

MethyLight method detects methylated alleles using methylation-specific PCR combined with TaqMan PCR. It is capable of highly sensitive detection of methylation, and is useful in detection of methylation from small amount of specimen (see, Methods. 2001 December; 25(4):456-62).

When using methylation-specific PCR, bisulfite sequencing, pyro-sequencing, COBRA and MethyLight, an unmethylated cytosine is specifically converted to an uracil whereas a methylated cytosine is not converted to an uracil due to bisulfite treatment. Accordingly, among the CpG islands in the promoter region of the miR-34b gene and/or miR-34c gene, the region of SEQ ID NO:6, 7 or 8 is converted to SEQ ID NO:9, 12 or 16, respectively, due to bisulfite treatment.

Accordingly, when the method of the present invention is practiced by bisulfite sequencing using, for example, the region described in SEQ ID NO:6 as the CpG island in the promoter region of miR-34b gene and/or miR-34c gene, the sample is treated with bisulfite to convert the sequence of SEQ ID NO:6 in the sample to a sequence of SEQ ID NO:9, and the methylated CpGs in this bisulfite-treated sequence can be detected by performing sequencing using:

```
a forward primer:              (SEQ ID NO: 10)
5'-GTTTTAAGAATTTGGGTTTTTATTTTTTAG-3'
and a reverse primer:              (SEQ ID NO: 11)
5'-CAAACTTCAATTCCCAACCCCAAAC-3'.
```

Alternatively, when the method of the present invention is practiced by pyro-sequencing using, for example, the region described in SEQ ID NO:7 as the CpG island in the promoter region of miR-34b gene and/or miR-34c gene, the sample is treated with bisulfite to convert the sequence of SEQ ID NO:7 in the sample to a sequence of SEQ ID NO:12, and the methylated CpGs in this bisulfite-treated sequence can be detected by performing PCR using:

```
a forward primer:              (SEQ ID NO: 13)
5'-TTAGTTTTTAGTTTTAAATTTTAGAGTTGG-3'
and a reverse primer:              (SEQ ID NO: 14)
5'-TCTCCCTTAAAAACCCTTCAAAAACC-3',
``` and further sequencing using:

```
a sequencing primer:    (SEQ ID NO: 15)
5'-TAATYGTTTTTGGAATTT-3'.
```

When DNA methylation analysis is performed by pyro-sequencing using foregoing primers, the antisense chain obtained by treating the sequence of SEQ ID NO:7 with bisulfite (a nucleotide sequence of SEQ ID NO:12) is amplified for the analysis. Because bisulfite treatment unties the double-strand of a DNA into single-strands before converting cytosines into uracils, the DNA after the treatment no longer has a complementarity, and the PCR products based on the sense chain and antisense chain after the treatment are partly different in their sequences. This is a phenomenon due to the chemical characteristics of bisulfite treatment, and the analytical result should theoretically be identical using either chain for performing PCR. A PCR primer is normally designed based on the nucleotide sequence of the sense chain of a gene. However, when there are any difficulties in PCR amplification or sequencing due to some reasons such as the presence of many repeat sequences, such technical difficulties may to be removed by designing primers based on the nucleotide sequence of the antisense chain, and pyro-sequencing above is one example of such case (see, Working Example 7).

Accordingly, in the example of pyro-sequencing above, the aforementioned forward primer (sense primer: SEQ ID NO:13) consists of a sequence on the antisense side to the nucleotide sequence of the CpG island in the promoter region of miR-34b gene and/or miR-34c gene described in SEQ ID NO:7. Similarly, the aforementioned reverse primer (antisense primer: SEQ ID NO:14) consists of a sequence on the sense side to the nucleotide sequence of the CpG island in the promoter region of miR-34b gene and/or miR-34c gene described in SEQ ID NO:7. Moreover, the aforementioned sequencing primer (SEQ ID NO:15) consists of a sequence on the antisense side to the nucleotide sequence of the CpG island in the promoter region of miR-34b gene and/or miR-34c gene described in SEQ ID NO:7.

Furthermore, when the method of the present invention is practiced by methylation-specific PCR using, for example, the region described in SEQ ID NO:8 as the CpG island in the promoter region of miR-34b gene and/or miR-34c gene, the sample is treated with bisulfite to convert the sequence of SEQ ID NO:8 in the sample to a sequence of SEQ ID NO:16, and the methylated CpGs in this bisulfite-treated sequence can be detected based on the presence or absence of a methylation-specific band or unmethylation-specific band, by performing the methylation-specific reaction using:

```
a for-                         (SEQ ID NO: 17)
ward primer:
5'-ATTCGTTTCGTTTCGCGTTCGTTTC-3'
and a reverse p-                   (SEQ ID NO: 18)
rimer:
5'-CTAAAACTAACTCTCTCGACCCCG-3',
``` and further performing unmethylation-specific reaction using:

```
a forward primer:              (SEQ ID NO: 19)
5'-TTTTTATTTGTTTTGTTTTGTGTTTGTTTTG-3'
and a reverse primer:              (SEQ ID NO: 20)
5'-CCTAAAACTAACTCTCTCAACCCCA-3'.
```

In the present invention, the detection of methylated CpGs above can also be carried out using a pair of primer that is specific to the nucleotide sequence of the CpG island in the promoter region of miR-34b gene and/or miR-34c gene, for example, a sense primer comprising a part of a nucleotide sequence that is identical to or substantially identical to a nucleotide sequence of SEQ ID NO:5, 6, 7 or 8, and an antisense primer comprising a part of a nucleotide sequence that is complementary to a nucleotide sequence that is identical to or substantially identical to a nucleotide sequence of SEQ ID NO:5, 6, 7 or 8. Here, the nucleotide sequence that is substantially identical to the nucleotide sequence of SEQ ID NO:5, 6, 7 or 8 includes, for example, a nucleotide sequence having a homology of about 70% or more, preferably about 80% or more, more preferably about 90% or more, still more preferably about 95% or more, most preferably about 98% or more, to the nucleotide sequence of SEQ ID NO:5, 6, 7 or 8. The nucleotide length of said primer is, for example, 15 to 40 nucleotides, preferably 17 to 35 nucleotides.

Accordingly, in a preferred embodiment, the detection of methylated CpG above according to the present invention is performed using: a pair of primers specific to the nucleotide sequence of the CpG island in the promoter region of miR-34b gene and/or miR-34c gene, for example, a sense primer comprising successive 15 to 40 nucleotides of a nucleotide sequence that is identical to or substantially identical to a nucleotide sequence of SEQ ID NO:5, and an antisense primer comprising successive 15 to 40 nucleotides of a nucleotide sequence that is complementary to a nucleotide sequence that is identical to or substantially identical to a nucleotide sequence of SEQ ID NO:5, more preferably using a sense primer comprising successive 15 to 40 nucleotides of a nucleotide sequence that is identical to or substantially identical to a nucleotide sequence of SEQ ID NO:6, and an antisense primer comprising successive 15 to 40 nucleotides of a nucleotide sequence that is complementary to a nucleotide sequence that is identical to or substantially identical to a nucleotide sequence of SEQ ID NO:6, still more preferably using a sense primer comprising successive 15 to 40 nucleotides of a nucleotide sequence that is identical to or substantially identical to a nucleotide sequence of SEQ ID NO:7, and an antisense primer comprising successive 15 to 40 nucleotides of a nucleotide sequence that is complementary to a nucleotide sequence that is identical to or substantially identical to a nucleotide sequence of SEQ ID NO:7, and particularly preferably using a sense primer comprising successive 15 to 40 nucleotides of a nucleotide sequence that is identical to or substantially identical to a nucleotide sequence of SEQ ID NO:8, and an antisense primer comprising successive 15 to 40 nucleotides of a nucleotide sequence that is complementary to a nucleotide sequence that is identical to or substantially identical to a nucleotide sequence of SEQ ID NO:8.

Furthermore, in the present invention, when the sample is treated with bisulfite, a DNA region within the sample having a nucleotide sequence of SEQ ID NO:6, 7 or 8 is converted to a region having a nucleotide sequence of SEQ ID NO:9, 12 or 16, respectively. Therefore, the detection of methylated CpGs above according to the present invention can be performed using, preferably, a sense primer comprising successive 15 to 40 nucleotides of a nucleotide sequence that is identical to or substantially identical to a nucleotide sequence of SEQ ID NO:9, and an antisense primer comprising successive 15 to 40 nucleotides of a nucleotide sequence that is complementary to a nucleotide sequence that is identical to or substantially identical to a nucleotide sequence of SEQ ID NO:9, more preferably using a sense primer comprising successive 15 to 40 nucleotides of a nucleotide sequence that is identical to or substantially identical to a nucleotide sequence of SEQ ID NO:12, and an antisense primer comprising successive 15 to 40 nucleotides of a nucleotide sequence that is complementary to a nucleotide sequence that is identical to or substantially identical to a nucleotide sequence of SEQ ID NO:12, and particularly preferably using a sense primer comprising successive 15 to 40 nucleotides of a nucleotide sequence that is identical to or substantially identical to a nucleotide sequence of SEQ ID NO:16, and an antisense primer comprising successive 15 to 40 nucleotides of a nucleotide sequence that is complementary to a nucleotide sequence that is identical to or substantially identical to a nucleotide sequence of SEQ ID NO:16.

Examples of particularly preferable combination of primers used in the method of the present invention include:

a combination in which the sense primer is an oligonucleotide having a nucleotide sequence of SEQ ID NO:10, and the antisense primer is an oligonucleotide having a nucleotide sequence of SEQ ID NO:11;

a combination in which the sense primer is an oligonucleotide having a nucleotide sequence of SEQ ID NO:13, and the antisense primer is an oligonucleotide having a nucleotide sequence of SEQ ID NO:14;

a combination in which the sense primer is an oligonucleotide having a nucleotide sequence of SEQ ID NO:17, and the antisense primer is an oligonucleotide having a nucleotide sequence of SEQ ID NO:18; and a combination in which the sense primer is an oligonucleotide having a nucleotide sequence of SEQ ID NO:19, and the antisense primer is an oligonucleotide having a nucleotide sequence of SEQ ID NO:20.

Any one of the oligonucleotides having sequences of SEQ ID NOs:10, 11, 13, 14, 15, 17, 18, 19 and 20 may preferably be used for practicing the present invention, and in preferred embodiment, for practicing the method of the present invention by methylation-specific PCR, bisulfite sequencing and pyro-sequencing, COBRA and MethyLight methods. For instance, an analysis by bisulfite sequencing is carried out preferably using a combination of PCR primers of the oligonucleotides having nucleotide sequences of SEQ ID NOs:10 and 11; an analysis by pyro-sequence is carried out preferably using a combination of PCR primers of the oligonucleotides having nucleotide sequences of SEQ ID NOs:13 and 14. Also, an oligonucleotide having a nucleotide sequence of SEQ ID NO:15 is preferably used as a sequencing primer for pyro-sequencing. An analysis by methylation-specific PCR is carried out preferably using a combination of PCR primers of the oligonucleotides having nucleotide sequences of SEQ ID NOs:17 and 18 for methylation-specific reaction, and a combination of PCR primers of the oligonucleotides having nucleotide sequences of SEQ ID NOs:19 and 20 for unmethylation-specific reaction.

Furthermore, according to the present invention, a kit for cancer detection is provided, the kit comprising a pair of oligonucleotides which is a pair of primers that are specific to nucleotide sequences of a CpG island in a promoter region of miR-34 gene and/or miR-34c gene as reagents for detecting or quantitating the methylated CpGs in a biological sample collected from a subject.

The primers comprised in the kit for cancer detection and used for detecting or quantitating methylated CpGs include, for example, a sense primer comprising a part of a nucleotide sequence that is identical to or substantially identical to a nucleotide sequence of SEQ ID NO:5, 6, 7 or 8, and an antisense primer comprising a part of a nucleotide sequence that is complementary to a nucleotide sequence that is identical to or substantially identical to the nucleotide sequence of SEQ ID NO:5, 6, 7 or 8, respectively. Here, the nucleotide sequence that is substantially identical to the nucleotide sequence of SEQ ID NO:5, 6, 7 or 8 includes, for example, a nucleotide sequence having a homology of about 70% or more, preferably about 80% or more, more preferably about 90% or more, still more preferably about 95% or more, most preferably about 98% or more, to the nucleotide sequence of SEQ ID NO:5, 6, 7 or 8. The nucleotide length of said primer is, for example, 15 to 40 nucleotides, preferably 17 to 35 nucleotides.

Accordingly, in a preferred embodiment, the oligonucleotides contained in the kit of the present invention and used as the reagent for detecting or quantitating methylated CpGs are, for example, a sense primer comprising successive 15 to 40 nucleotides of a nucleotide sequence that is identical to or substantially identical to a nucleotide sequence of SEQ ID NO:5 and an antisense primer comprising successive 15 to 40 nucleotides of a nucleotide sequence that is complementary to a nucleotide sequence that is identical to or substantially identical to a nucleotide sequence of SEQ ID NO:5, preferably a sense primer comprising successive 15 to 40 nucleotides of a nucleotide sequence that is identical to or substantially identical to a nucleotide sequence of SEQ ID NO:6 and an antisense primer comprising successive 15 to 40 nucleotides of a nucleotide sequence that is complementary to a nucleotide sequence that is identical to or substantially identical to a nucleotide sequence of SEQ ID NO:6, more preferably a sense primer comprising successive 15 to 40 nucleotides of a nucleotide sequence that is identical to or substantially identical to a nucleotide sequence of SEQ ID NO:7 and an antisense primer comprising successive 15 to 40 nucleotides of a nucleotide sequence that is complementary to a nucleotide sequence that is identical to or substantially identical to a nucleotide sequence of SEQ ID NO:7, and particularly preferably a sense primer comprising successive 15 to 40 nucleotides of a nucleotide sequence that is identical to or substantially identical to a nucleotide sequence of SEQ ID NO:8 and an antisense primer comprising successive 15 to 40 nucleotides of a nucleotide sequence that is complementary to a nucleotide sequence that is identical to or substantially identical to a nucleotide sequence of SEQ ID NO:8.

The kit of the present invention for cancer detection is suitable for detecting methylated CpGs in a CpG island in a promoter region of miR-34b gene and/or miR-34c gene, and the method of detecting cancer according to the present invention can therefore be practiced using said kit.

Accordingly, the aforementioned primers can preferably be used for practicing the method of the present invention using such as methylation-specific PCR, bisulfite sequencing and pyro-sequencing, COBRA and MethyLight methods as above. When using these methods which involve bisulfite treatment of the sample, a DNA region having a nucleotide sequence of SEQ ID NO:6, 7 or 8 in the sample is converted, for example to a region having a nucleotide sequence of SEQ ID NO:9, 12 or 16, respectively. Therefore, in the kit of the present invention, examples of the oligonucleotides used as the reagents for detecting or quantitating methylated CpGs include, preferably, a sense primer comprising successive 15 to 40 nucleotides of a nucleotide sequence that is identical to or substantially identical to a nucleotide sequence of SEQ ID NO:9 and an antisense primer comprising successive 15 to 40 nucleotides of a nucleotide sequence that is complementary to a nucleotide sequence that is identical to or substantially identical to a nucleotide sequence of SEQ ID NO:9, more preferably a sense primer comprising successive 15 to 40 nucleotides of a nucleotide sequence that is identical to or substantially identical to a nucleotide sequence of SEQ ID NO:12 and an antisense primer comprising successive 15 to 40 nucleotides of a nucleotide sequence that is complementary to a nucleotide sequence that is identical to or substantially identical to a nucleotide sequence of SEQ ID NO:12, and particularly preferably a sense primer comprising successive 15 to 40 nucleotides of a nucleotide sequence that is identical to or substantially identical to a nucleotide sequence of SEQ ID NO:16 and an antisense primer comprising successive 15 to 40 nucleotides of a nucleotide sequence that is complementary to a nucleotide sequence that is identical to or substantially identical to a nucleotide sequence of SEQ ID NO:16.

Moreover, according to the invention, a kit for cancer detection is provided, the kit comprising one or more oligonucleotides having a nucleotide sequence of any one of SEQ ID NOs:10, 11, 13, 14, 15, 17, 18, 19 and 20 as reagents for detecting or quantitating methylated CpGs in a biological sample collected from a subject, and such kit can be used for practicing the method of the present invention.

Further, examples of particularly preferred combination of oligonucleotide contained in the kit of the invention include: the combination of an oligonucleotide having a nucleotide sequence of SEQ ID NO:10 and an oligonucleotide having a nucleotide sequence of SEQ ID NO:11; a combination of an oligonucleotide having a nucleotide sequence of SEQ ID NO:13 and an oligonucleotide having a nucleotide sequence of SEQ ID NO:14, or a combination of an oligonucleotide having a nucleotide sequence of SEQ ID NO:13, an oligonucleotide having a nucleotide sequence of SEQ ID NO:14 and an oligonucleotide having a nucleotide sequence of SEQ ID NO:15; a combination of an oligonucleotide having a nucleotide sequence of SEQ ID NO:17 and an oligonucleotide having a nucleotide sequence of SEQ ID NO:18; and a combination of an oligonucleotide having a nucleotide sequence of SEQ ID NO:19 and an oligonucleotide having a nucleotide sequence of SEQ ID NO:20.

The foregoing oligonucleotides can be used for practicing the method of the present invention by methylation-specific PCR, bisulfite sequencing and pyro-sequencing, COBRA and MethyLight methods as described above. Therefore, when the kit of the invention is aimed for an analysis by bisulfite sequencing, for example, it preferably comprises a combination of PCR primers of the oligonucleotides having nucleotide sequences of SEQ ID NOs:10 and 11, when the kit is aimed for an analysis by pyro-sequencing, it preferably comprises a combination of PCR primers of the oligonucleotides having nucleotide sequences of SEQ ID NOs:13 and 14. Also, the kit may comprise an oligonucleotide having a nucleotide sequence of SEQ ID NO:15 as a sequencing primer for pyro-sequencing. When the kit is aimed for an analysis by methylation-specific PCR, it is preferred that the kit comprises a combination of PCR primers of the oligonucleotides having nucleotide sequences of SEQ ID NOs:17 and 18 for methylation-specific reaction and a combination of PCR primers of the oligonucleotides having nucleotide sequences of SEQ ID NOs:19 and 20 for unmethylation-specific reaction.

The kit of the present invention for cancer detection may be in any form, as long as it comprises one or more of aforementioned oligonucleotides or primers, and may appropriately comprise reagents, apparatuses, instruction, etc., and may comprise one or more of solutions and apparatuses used for DNA extraction from a biological sample such as tissue or cells (e.g., buffers for tissue- or cell-lysis, phenol/chloroform, ethanol, etc.), reagents necessary for PCR (e.g., $H_2O$, buffer, $MgCl_2$, dNTP mixture, Taq polymerase, etc.), reagents necessary for quantitation of PCR-amplified fragments (e.g., RI, fluorescent dye, etc.).

Also, in the present invention, a cancer refers to a malignant tumor and encompasses those which are generally included within the concept of cancer.

Moreover, a colorectal cancer encompasses those which are generally included in the concept of colorectal cancer, including malignant tumors generated from epithelial mucosa of large intestine, as well as colon adenoma. A gastric cancer encompasses those which are generally included within the concept of gastric cancer, including malignant tumors generated from epithelial mucosa of stomach. Further, a pancreatic cancer encompasses those which are generally included within the concept of pancreatic cancer.

Furthermore, a breast cancer encompasses those which are generally included within the concept of breast cancer, meaning malignant tumors generated on mammary gland, fat layer and skin, including invasive breast cancer, non-invasive breast cancer, and those classified as Paget's disease.

In the present invention, as a "biological sample obtained from the subject", for example, blood, serum, ascites, urine, stool, gastric lavage fluid, pancreatic juice, bile, or digestive tract tissue (stomach, small intestine, large intestine, pancreas, etc.), tissue which constitutes a breast such as mammary gland, fat layer or skin, secretion secreted from mammary gland, lavage fluid secreted from mammary gland (ductal fluid) may be utilized without specific limitation as long as detection of cancer is possible. The expression levels of miR-34b gene and/or miR-34c gene are generally high in any normal tissue and tend to be markedly decreased in tumor tissue. Therefore, biological sample obtained from the subject may appropriately be selected according to the object. For instance, when the object is to detect a colorectal cancer, the biological sample is preferably serum, stool or tissue of large intestine; when the object is to detect a gastric cancer, the sample is preferably serum, gastric lavage fluid or stomach tissue; when the object is to detect a pancreatic cancer, the sample is preferably serum, pancreatic juice or pancreatic tissue; when the object is to detect a breast cancer, the sample is preferably serum, tissues such as mammary gland, fat layer or skin which constitutes breast, secretion secreted from mammary gland, lavage fluid secreted from mammary gland (ductal fluid); and when the object is to detect a bile duct cancer or gallbladder cancer, the sample is preferably serum, bile, bile duct tumor tissue or gallbladder tumor tissue.

Also, the biological sample that can be used in the method of the present invention may be collected by any means, for example, it may be collected by surgery, may be collected by paracentesis needle for tissue collection, or may be collected as pancreatic juice, bile, or gastric lavage fluid, secretion secreted from mammary gland or lavage fluid secreted from mammary gland (ductal fluid).

In practicing the method of the present invention, although it is possible to directly carry out the detection of methylated CpGs without any preliminary treatments, such as DNA extraction, to the biological sample obtained from the subject, it is preferred to extract DNA in the biological sample before detecting methylated CpGs by aforementioned method, e.g., methylation-specific PCR, bisulfite sequencing, pyro-sequencing, COBRA or MethyLight. Methods of extracting DNA from biological sample are well known in the art, and may be performed using, for example, phenol/chloroform, ethanol, or commercially available DNA extraction reagents.

Furthermore, the inventors have discovered that miR-34b and/or miR-34c exhibit a high expression level in normal tissue while their expression is markedly suppressed in tumor tissue, and that they suppress oncogenes such as MYB gene and MET gene and cell-cycle regulatory genes such as CDK4 gene. Accordingly, since miR-34b and/or miR-34c are considered to be effective for suppressing proliferation or metastasis of cancer cells, the present invention also provides a therapeutic agent for cancer comprising miR-34b and/or miR-34c, as well as a therapeutic agent for cancer comprising a nucleic acid encoding miR-34b gene and/or miR-34c gene.

Here, as mentioned above, miR-34b includes specifically an RNA encoded by a DNA sequence that is identical to or substantially identical to a DNA sequence of SEQ ID NO:1 (precursor miRNA-34b), as well as an RNA having a RNA nucleotide sequence that is identical to or substantially identical to an RNA sequence of SEQ ID NO:2 (matured type miRNA-34b), and miR-34c includes specifically an RNA encoded by a DNA sequence that is identical to or substantially identical to a DNA sequence of SEQ ID NO:3 (precursor miRNA-34c), as well as an RNA having a RNA nucleotide sequence that is identical to or substantially identical to an RNA sequence of SEQ ID NO:4 (matured type miRNA-34c).

Also, a nucleic acid encoding miR-34b gene includes, for example, a DNA comprising a nucleotide sequence of SEQ ID NO:1 or a DNA comprising a nucleotide sequence that hybridizes to the nucleotide sequence of SEQ ID NO:1 under a stringent condition and encoding a miRNA having substantially equal properties to a miRNA comprising a nucleotide sequence of SEQ ID NO:2. Similarly, a nucleic acid encoding miR-34c gene includes, for example, a DNA comprising a nucleotide sequence of SEQ ID NO:3 or a DNA comprising a nucleotide sequence that hybridizes to the nucleotide sequence of SEQ ID NO:3 under a stringent condition and encoding an miRNA having substantially equal properties to a miRNA comprising the nucleotide sequence of SEQ ID NO:4. Here, as a DNA comprising a nucleotide sequence that specifically hybridizes to the nucleotide sequence of SEQ ID NO:1 or 3 under a stringent condition, a DNA comprising a nucleotide sequence having homology of about 60% or more, preferably about 70% or more, more preferably about 80% or more, still more preferably about 90% or more, particularly preferably about 95% or more, most preferably about 98% or more, to a nucleotide sequence that is complementary to the nucleotide sequence of SEQ ID NO:1 or 3 may be used, for example.

In addition, the inventors have discovered that the CpG island present in the promoter region of miR-34b gene and/or miR-34c gene has an activity as the promoter of BTG4 (B cell translocation gene 4) gene which is encoded in opposite direction (antisense direction) to miR-34b gene and/or miR-34c gene on the same chromosome, and that BTG4 has a function of suppressing cell proliferation, and that its expression level is high in normal tissues but markedly suppressed in cancer cells. Accordingly, since BTG4 is considered to be capable of suppressing proliferation or metastasis of tumor cells, a therapeutic agent for cancer comprising BTG4 as well as a therapeutic agent for cancer comprising nucleic acid encoding BTG4 gene are provided according to the present invention.

Here, BTG4 used in the present invention is a protein called as B cell translocation gene 4 (also known as PC3B or MGC33003) (accession number NM_017589), and includes, for example, a protein comprising an amino acid sequence that is identical to or substantially identical to an amino acid sequence of SEQ ID NO:21. Here, an example of an amino acid sequence that is substantially identical to an amino acid sequence of SEQ ID NO:21 includes an amino acid sequence having homology of about 70% or more, preferably about 80% or more, more preferably about 90% or more, still more preferably about 95% or more, most preferably about 98% or more to an amino acid sequence of SEQ ID NO:21. Also, in the present invention, among the polypeptides in which the amino acid sequence encompassed by BTG4 has a substantially identical amino acid sequence to the polypeptide of SEQ ID NO:21, preferably used are those which maintain, as functions of BTG4, the properties and functions of the protein consisting of an amino acid sequence of SEQ ID NO:21 (e.g., cancer cell proliferation suppressing effect) at equal level to a protein substantially consisting of an amino acid sequence.

Further, the nucleic acid encoding BTG4 gene used in the present invention includes, for example, a nucleic acid encoding a protein having an amino acid sequence that is identical to or substantially identical to an amino acid sequence of SEQ ID NO:21, as well as a DNA comprising a nucleotide sequence of SEQ ID NO:22, or a DNA comprising a nucleotide sequence that specifically hybridizes to a nucleotide sequence of SEQ ID NO:22 under a stringent condition and encodes a protein having a substantially equal properties to the protein consisting of the amino acid sequence of SEQ ID NO:21 (e.g., cancer cell proliferation suppressing effect, etc.). Here, as a DNA comprising a nucleotide sequence that specifically hybridizes to a nucleotide sequence of SEQ ID NO:22 under a stringent condition, a DNA comprising a nucleotide sequence having homology of about 60% or more, preferably about 70% or more, more preferably about 80% or more, still more preferably about 90% or more, particularly preferably about 95% or more, most preferably about 98% or more to a nucleotide sequence that is complementary to a nucleotide sequence of SEQ ID NO:22, for example, may be used.

Although the nucleotide sequence of BTG4 gene may differ not only between different species but also even within the same species, due to polymorphism, isoforms, etc., a gene having different nucleotide sequence is still encompassed by BTG4 gene as long as it encodes BTG4.

The above-mentioned cancer therapeutic agent according to the present invention may be used for any cancer, although it is particularly preferably used for colorectal cancer, gastric cancer, pancreatic cancer and breast cancer as mentioned above.

The cancer therapeutic agent of the present invention may be provided as a therapeutic agent for cancer being formulated in combination with pharmaceutically acceptable carriers (e.g., excipient, binder, disintegrant, lubricant, stabilizer, antiseptic, pH adjusting agent, flavoring agent, diluent, solvent for injection, etc.). The therapeutic agent of the present invention may also comprise tag or nanocapsule that enable specific delivery to target tissue. The therapeutic agent of the present invention may comprise any one of miR-34b, a nucleic acid encoding miR-34b, miR-34c, a nucleic acid encoding miR-34c, BTG4 and a nucleic acid encoding BTG4 gene alone or in combination of two or more.

Furthermore, the therapeutic agent of the present invention may further comprise other pharmaceutically active ingredient such as a known anticancer agent effective in the therapy of cancer (e.g., fluorouracil, tamoxifen, anastrozole, aclarubicin, doxorubicin, tegafur, cyclophosphamide, irinotecan, cytarabine, paclitaxel, docetaxel, epirubicin, carboplatin, cisplatin, thiotepa, or a pharmaceutically acceptable salt thereof), or may be used in combination with such active ingredient.

The route of administration of the therapeutic of the present invention includes, for example, oral administration, parenteral administration (such as intravenous administration, intraarterial administration, subcutaneous administration, intramuscular administration, intraperitoneal administration, topical administration), and examples of the dosage form include spray, capsules, tablets, granules, syrup, emulsion, suppository, injection and suspension. Specifically, in the case of topical administration, the diseased area is exposed by surgery, and the therapeutic agent of the present invention can directly be administered to the tumor tissue by means of injection, etc. In the case of non-topical administration, the administration may be carried out through tumor feeding vessels. Preferred route of administration is topical administration.

In particular, the therapeutic agent of the present invention comprising a nucleic acid encoding miR-34b, a nucleic acid encoding miR-34c or a nucleic acid encoding BTG4 gene may be used as a gene therapy agent aimed to introduce and express miR-34b gene, miR-34c gene or BTG4 gene, respectively, in a cancer cell.

The cancer therapeutic agent of the present invention used as a gene therapy agent may be parenterally administered to a subject by HVJ liposome method, a method in which the nucleotide sequence of said gene is directly administered by injection, calcium phosphate method, DEAE-dextran method, electroporation method, a method using gene gun, method of administration by lipofection, a method using appropriate expression vector (e.g., and adenovirus vector, adeno-associated virus vector, herpes virus vector, vaccinia virus vector, retrovirus vector, etc.).

Although the dosage and frequency of administration of the cancer therapeutic agent of the present invention vary depending on the effect to be achieved, the method of administration, the duration of the therapy, the age, body weight or gender of the subject, when miR-34b and/or miR-34c or BTG4 is used, the dosage may appropriately be chosen normally in the range of 100 µg to 100 mg, preferably 1 to 20 mg, per 1 day for an adult in the case of human, and when a nucleic acid encoding miR-34b, a nucleic acid encoding miR-34c or a nucleic acid encoding BTG4, or an expression vector comprising one of these is used, the dosage may appropriately be chosen normally in the range of 0.01 mg/kg to 1 g/kg, preferably 0.1 mg/kg to 500 mg/kg per day for an adult in the case of human, and the frequency of administration may appropriately be chosen from once to several times a day. The dosage, however, may vary depending on various conditions, and is therefore not limited to the range above.

Furthermore, according to the present invention, use of miR-34b, a nucleotide encoding miR-34b gene, miR-34c, a nucleotide encoding miR-34c gene, BTG4, or a nucleotide encoding BTG4 gene, in particular use in production of a therapeutic agent according to the present invention and use as a therapeutic agent according to the invention are provided.

Furthermore, according to the present invention, a method of cancer treatment comprising administrating miR-34b, a nucleotide encoding miR-34b gene, miR-34c, a nucleotide encoding miR-34c gene, BTG4, or a nucleotide encoding BTG4 gene is provided. The effective dosage, method for administration and dosage form in this case may be pursuant to the description above.

WORKING EXAMPLES

The present invention is illustrated in more detail using following working examples, although the scope of the present invention is not limited by these examples.

Working Example 1

Expression Analysis of miRNAs

In order to identify miRNAs that undergo epigenetic silencing in a cancer cell, miRNA was collected from a cancer cell line HCT116 cell, a HCT116 cell treated with DNA methyltransferase inhibitor 5-aza-2'-deoxycytidine (DAC) (2 µM, 72 hours), and a HCT116 cell in which two DNA methyltransferase genes DNMT1 and DNMT3B genes have been knocked out (hereinafter may also be referred to as DKO2 cell; it is known that DNA methylation has almost been lost throughout the genome in this cell) using mirVana miRNA isolation kit (Ambion) or Trizol (Invitrogen), and the expression levels of 157 miRNAs were compared by delta/delta CT method using TaqMan miRNA Assay System (Applied Biosystems) and ABI 7900 real-time PCR analyzer (Applied Biosystems). U6 snRNA were used as an internal control.

The expression level of each miRNA was converted to the ratio of the expression level of each miRNA to that of U6 snRNA (i.e., the expression level of each miRNA/the expression level of U6 snRNA) and analyzed. As shown in FIG. 2 (in FIG. 2, for each miRNA, the top bar indicates HCT116 cell (HCT116), the second bar indicates the HCT116 cell with DAC treatment (HCT116+DAC), the third bar indicates the HCT116 cell in which DNA methyltransferase genes are knocked out (DNMT knockout)), it has been revealed that the treatment with DNA methyltransferase inhibitor and the knockout of DNA methyltransferase genes induced the expression of 37 miRNAs (hsa-miR-34b, hsa-miR-34c, hsa-miR-105, hsa-miR-124a, hsa-miR-124b, hsa-miR-127, hsa-miR-129, hsa-miR-134, hsa-miR-137, hsa-miR-138, hsa-miR-142-3p, hsa-miR-142-5p, hsa-miR-146, hsa-miR-150, hsa-miR-154, hsa-miR-154*, hsa-miR-155, hsa-miR-184, hsa-miR-187, hsa-miR-199a, hsa-miR-205, hsa-miR-296, hsa-miR-299, hsa-miR-302a, hsa-miR-302b, hsa-miR-302c, hsa-miR-302d, hsa-miR-323, hsa-miR-337, hsa-miR-338, hsa-miR-367, hsa-miR-368, hsa-miR-370, hsa-miR-371, hsa-miR-372, hsa-miR-373 and hsa-miR-373*).

Among these 37 miRNAs identified as above, it has been known that, for miR-34b and miR-34c, a single precursor RNA transcribed from chromosome 11q23 is processed to generate each mature miRNA. It is understood that although the expression levels of miRNA34b and miR-34c are both extremely low in the HCT116 cell (HCT116), the treatment with DNA methyltransferase inhibitor (HCT116+DAC) restores their expression, and they are observed to be highly expressed in the DKO2 cell (DKO2). Almost similar patterns of induction were shown in miR-34b and miR-34c (FIG. 3A).

Working Example 2

Expression Analysis of miR-34b and miR-34c in Colorectal Cancer Cell Lines

Furthermore, in order to examine whether the induction of expression of miR-34b and miR-34c (hereinafter may also be referred to as miR-34b/c) is observed in colorectal cancer cell lines other than HCT116 cell, for 9 colorectal cancer cell lines (CaCO2, Colo320, DLD1, HCT116, HT29, LoVo, RKO, SW48 and SW480) and the same 9 colorectal cancer cell lines with DAC treatment, miRNA was collected using mirVana miRNA isolation kit (Ambion) or Trizol (Invitrogen), and the expression levels of miR-34 b/c were analyzed by delta/delta CT methods using TaqMan miRNA Assay System (Applied Biosystems) and ABI 7900 real-time PCR analyzer (Applied Biosystems). DKO2 cell was used as a control, and U6 snRNA was used as an internal control.

The expression level of miRNA was converted to the ratio of the expression level of each miRNA to that of U6 snRNA (i.e., the expression level of each miRNA/the expression level of U6 snRNA) and analyzed. As shown in FIG. 4 (indicated as an average and standard deviation of three repeated experiments), it was revealed that DAC treatment (DAC+) induces the expression of miR-34b (FIG. 4A) and miR-34c (FIG. 4B) in all said 9 colorectal cancer cell lines. It is therefore suggested that the expression of miR-34b/c genes may be suppressed through the epigenetic silencing by DNA methylation.

Working Example 3

Analysis of miR-34b/c Gene as a p53 Target

Because miR-34b gene and miR-34c gene overlap intron 1 and exon 1 of a non-coding RNA BC021376, this BC021376 is considered to be a candidate precursor RNA of miR-34b/c. Furthermore, there is a binding sequence for p53, a tumor suppressor gene product, immediately close to the transcription initiation site of BC021736. Also, there is another gene B-cell translocation gene 4 (BTG4) being encoded in antisense direction to miR-34b/c, and a CpG island being located close to BTG4 exon 1 and miR-34 b/c (FIG. 3B).

Thus, firstly, a HCT116 cell or p53-knockout HCT116 cell was treated either with DAC alone (2 µM, 72 hours), with DAC (2 µM, 72 hours) and then further with adriamycin (ADR: 0.5 µg/ml, 24 hours) which is known to induce p53, or with adriamycin alone (0.5 µg/ml, 24 hours), and their miR-34b/c expression levels were analyzed by delta/delta CT method using TaqMan miRNA Assay System (Applied Biosystems) and ABI 7900 real-time PCR analyzer (Applied Biosystems). U6 snRNA was used as an internal control.

As shown in FIG. 5A (indicated by the average and standard deviation of three repeated experiments), an induction of miR-34b/c expression was observed in the HCT116 cell treated either with DAC at low concentration or with ADR, whereas miR-34b/c expression was synergistically increased when treated with both DAC and ADR.

Furthermore, as shown in FIG. 5B (indicated by the average and standard deviation of three repeated experiments), in the HCT116 cell in which p53 gene has been knocked out, miR-34b/c expression was induced when the cell was treated with DAC, but not at all when the cell was treated with ADR. When the cell was treated with both DAC and ADR, the miR-34b/c expression was induced only at a similar level to the case when the cell was treated with DAC alone.

Then, similarly, a HCT116 cell or a HCT116 cell in which p53 gene has been knocked out was treated either with DAC alone (2 µM, 72 hours), with DAC (2 µM, 72 hours) and then further with ADR (0.5 µg/ml, 24 hours), or with ADR alone (0.5 µg/ml, 24 hours), and the induction of p53 expression was analyzed at protein level by western-blotting using an anti-p53 antibody. The expression of β-actin was confirmed as control, and the expression of p21 gene which is known as a representative target of p53 was similarly confirmed.

The results, as shown in FIG. 5C, indicated that in the HCT116 cell (WT) p53 expression was induced by ADR treatment but not by DAC treatment, and that the expression of p21 gene, a p53 target, was also induced in similar pattern to that of p53. On the other hand, in the HCT116 cell in which p53 has been knocked out (p53KO), neither p53 nor p21 was changed at all by either treatment.

Then, a p53 binding sequence (SEQ ID NO:23), which is located in a region close to miR-34b/c gene, was inserted into pGL3-promoter (Promega), a luciferase vector with SV40 promoter, to generate a vector (pGL3-promoter-p53RE) (FIG. 6A). This pGL3-promoter-p53RE was co-transfected into a HCT116 cell with p53-expressing vector, then 48 hours after transfection, luciferase activity was measured, showing an increased activity (FIG. 6B).

These results confirmed that miR-34b/c gene is a target of p53 gene and its expression is controlled by both p53 and epigenetic gene silencing.

Working Example 4

Promoter Analysis of miR-34b/c Gene

There is a CpG island located near miRNA-34b/c gene (FIG. 7). Because the fourth lysine of histone H3 (H3-K4) is trimethylated in general at the RNA transcription initiation site, the trimethylation of H3-K4 is known to be an index of transcription initiation site. Thus, in order to investigate whether the CpG island near miR-34b/c gene is the transcription initiation site of miR-34b/c gene, we analyzed the H3-K4 trimethylation within the area to 4.5 kb upstream of miRNA-34b/c for a HCT116 cell, a HCT116 cell with DAC treatment (2 µM, 72 hours) and a DKO2 cell, by chromatin immunoprecipitation using Chromatin Immunoprecipitation kit (Upstate). Specifically, cells were fixed in formalin and dissolved in an elution buffer. DNA was homogenized by a homogenizer and then subjected to immunoprecipitation with H3-K4 antibody. Precipitated DNA was detected by PCR. The results, as shown in FIG. 7, show H3-K4 trimethylation consistent with the CpG island in the sequence near miR-34b/c gene as shown in the horizontal axis (see, FIG. 7, top panel: the schematic diagram of the sequence near miR-34b/c gene), suggesting the presence of transcription initiation site of miR-34b/c gene near this CpG island.

This CpG island near miR-34b/c is encoding a miR-34b/c gene in telomere-ward direction, and also encoding another gene, B-cell translocation gene 4 (BTG4) gene, in centromere-ward direction. An analysis using a promoter region predicting program (WWW Promoter Scan, http://www-bimas.cit.nih.gov/molbio/proscan/) suggested that this CpG island has promoter activity in both direction. This CpG island region was thus cloned, and the miR-34b/c-ward sequence of SEQ ID NO:24 and the BTG4-ward sequence of SEQ ID NO:25 were inserted into a luciferase vector pGL3-Basic (Promega) to produce pGL3miR-34b vector and pGL3-BTG4 vector, respectively, which were introduced into colorectal cancer cell lines HCT116 and DLD1 cell, and the promoter activity of each sequence was measured 48 hours after transfection. The results, as shown in FIG. 8B, indicate that luciferase activity was increased in both cell, transfected either with pGL3-miR34b or pGL3-BTG4, compared to the case when the cells were transfected with pGL3-Basic, a luciferase vector without a promoter used as negative control, confirming that the CpG island near miR-34b/c gene has promoter activity in both miR-34b/c gene direction and BTG4 gene direction.

Working Example 5

DNA Methylation Analysis by Methylation-Specific PCR (MSP)

DNA methylation of a CpG island in a promoter region of miR-34b/c gene was analyzed by methylation-specific PCR (MSP) method for 9 colorectal cancer cell lines (CaCO2, Colo320, DLD1, HCT116, HT29, LoVo, RKO, SW48 and SW480) as well as DKO2 cell and human normal colon tissue. Specifically, bisulfite treatment was performed using EpiTect Bisulfite Kits (Qiagen), and the methylation was detected thereafter with methylation specific primers:

```
5'-ATTCGTTTCGTTTCGCGTTCGTTTC-3'   (SEQ ID NO: 17)
and

5'-CTAAAACTAACTCTCTCGACCCCG-3',   (SEQ ID NO: 18)
``` and unmethylation was detected with unmethylation specific primers:

```
                                  (SEQ ID NO: 19)
    5'-TTTTTATTTGTTTTGTTTTGTGTTTGTTTTG-3'
    and (SEQ ID NO: 20)
    5'-CCTAAAACTAACTCTCTCAACCCCA-3'.
```

The primers were designed to specifically amplify the part of the CpG island indicated with heavy line in FIG. 8A (the region consisting of the nucleotide sequence of SEQ ID NO:8).

As a result, as shown in FIG. 9A, definite bands were detected from the specific amplification of methylated site (M) but vanishingly little from the specific amplification of unmethylated site (U) in all 9 colorectal cancer cell lines, confirming a high-level DNA methylation in the CpG island in the promoter region of miR-34b/c gene. On the other hand, in DKO2 cell in which DNMT gene has been knocked out and in normal colon tissue, methylation-specific bands were hardly detected (M) but unmethylation-specific bands were strongly detected (U), confirming that the CpG island in the promoter region of miR-34b/c gene was methylated very little (FIG. 9A).

Then, 126 clinical samples of colorectal cancer were obtained as frozen tissues by surgery. Of those 97 were provided with information about age (average age=65.3 years old) and 102 cases were provided with information about gender (male 67 cases and female 35 cases). DNA was extracted and the methylation of the CpG island in the promoter region of miR-34b/c gene was analyzed as above by methylation-specific PCR (MSP).

The result shows that the DNA methylation of the CpG island was detected in many samples in tumor colon tissue (T), but none or very slightly if any in control non-tumor colon tissue (N), as shown in 7 samples (CRC1 to CRC7) in FIG. 9B. Further, as shown in FIG. 9C, in 114 among said 126 cases (90%), DNA methylation was detected in the CpG island in the promoter region of miR-34b/c gene.

These results suggested that the CpG island in the promoter region of miR-34b/c gene is specifically methylated in colorectal cancer cell and tissue.

Working Example 6

DNA Methylation Analysis by Bisulfite Sequencing

The methylation of the CpG island in the promoter region of miR-34b/c was analyzed for colorectal cancer cell lines HCT116 cell (HCT116) and DKO2 cell (DKO2), normal human colon tissue (normal colon), human colon tumor tissue (Tumor#1 and Tumor#2) (frozen tissue obtained by surgery, same tissue as used in Working Example 5) by bisulfite sequencing. Specifically, DNA was bisulfite-treated using EpiTect Bisulfite Kits (Qiagen), before PCR amplification of the interested region using primers for bisulfite sequencing:

```
                                  (SEQ ID NO: 10)
    5'-GTTTTAAGAATTTGGGTTTTTATTTTTTAG-3'
    and (SEQ ID NO: 11)
    5'-CAAACTTCAATTCCCAACCCCAAAC-3'.
```

Amplified PCR products were then cloned with TOPO TA Cloning Kit (Invitrogen), and their nucleotide sequences were analyzed by ABI 3130x sequencer (Applied Biosystems). Primers were designed to specifically amplify the heavy-lined part indicated as "bisulfite seq" in the CpG island in FIG. 8A (the region consisting of a nucleotide sequence of SEQ ID NO:6).

As a result, as shown in FIG. 10 (in FIG. 10 the horizontal axis indicates the number of CpG sequences and the vertical axis indicates the number of clones analyzed), among 22 CpGs located in the area of about 200 bps, all CpGs were highly methylated in colorectal cancer cell line HCT116 cell (HCT116), whereas the methylation was almost completely lost in all sites in DKO2 cell (DKO2) which is a HCT116 cell in which DNMT gene has been knocked out, the result being completely consistent with the result of the analysis by MSP method in Working Example 5 above. Furthermore, in colon tumor tissue (Tumor#1 and Tumor#2) almost all CpGs were highly methylated, whereas in normal colorectal tissue (normal colon) only a few CpGs were slightly methylated. The level of methylation in colon tumor tissue was lower than that in the HCT116 cell, showing a mixed pattern of methylation with unmethylation, which is considered to be due to the mixed presence of cancer and non-cancer cells within tissue.

Working Example 7

DNA Methylation Analysis by Pyro-Sequencing

DNA methylation of the CpG island in the promoter region of miR-34b/c was quantitatively analyzed for colorectal cancer cell line HCT116 cell and DNMT gene-knockout DKO2 cell, human normal colon tissue (normal colon), human colon tumor tissue (Tumor#1 (same tissue as Working Example 6 above)) by pyro-sequencing. Specifically, DNA was bisulfite-treated using EpiTect Bisulfite Kits (Qiagen) before PCR amplification of the interested region using primers for pyro-sequencing:

```
                                          (SEQ ID NO: 13)
    5'-TTAGTTTTTAGTTTTAAATTTTAGAGTTGG-3'
    and (SEQ ID NO: 14)
    5'-TCTCCCTTAAAAACCCTTCAAAAACC-3',
``` followed by sequence analysis using Pyro Gold reagent (Biotage) and the primer for sequencing (5'-TAATYGTTTTTGGAATTT-3' (SEQ ID NO:15)). Primers were designed to specifically amplify the heavy-lined part indicated as "pyro seq" in the CpG island in FIG. 8A (the region consisting of a nucleotide sequence of SEQ ID NO:7).

Besides, this example of pyro-sequencing is aimed to perform an analysis by specifically amplifying a region having a nucleotide sequence of SEQ ID NO:7. However, when the primers used were designed based on the sense chain of the bisulfite-treated DNA of the region having a nucleotide sequence of SEQ ID NO:7, sequencing reaction was difficult due to the presence of many repeat sequences, etc. Thus, the analysis of DNA methylation of the region of interest of SEQ ID NO:7 was achieved using primers that were designed based on the sequence of the antisense chain of the bisulfite-treated DNA of the region having the nucleotide sequence of SEQ ID NO:7 (a sequence having a nucleotide sequence of SEQ ID NO:12).

The result, as shown in FIG. 11 (in FIG. 11, the horizontal axis indicates nucleotide sequence, the vertical axis indicates fluorescent intensity, i.e., methylation intensity), was consistent with the results of analyses by MSP and bisulfite-sequencing.

Furthermore, 17 samples of normal colon tissue (normal colon), 10 samples of colon tumor tissue (tumor (U)) that was determined as methylation-negative in MSP analysis in Working Example 5, 101 samples of colon tumor tissue (tumor (M)) that was determined as methylation-positive in MSP analysis in Working Example 5, and 9 colorectal cancer cell lines (CaCO2, Colo320, DLD1, HCT116, HT29, LoVo, RKO, SW48 and SW480) (cell lines) were analyzed by pyro-sequencing as above. The results are shown in FIG. 12.

In the graph of FIG. 12, each one dot indicates one sample, and the vertical axis indicates the level of methylation. As understood from FIG. 12, the results were similar to those obtained by MSP and bisulfite sequencing, confirming that pyro-sequencing is capable of being used for a high-throughput and quantitative analysis of DNA methylation.

Moreover, 16 gastric cancer cell lines (MKN1, MKN7, MKN74, SH101, SNU1, SNU638, JRST, KatoII, AZ521, MKN28, MKN45, NUGC3, NUGC4, AGS, NCI-N87, SNU16), 9 pancreatic cancer cell lines (BxPC-3, Capan2, CFPAC, KLM-1, KP1-NL, MIAPaCa, Panc-1, PK-8, PK-9), 9 breast cancer cell lines (MCF7, MDA-MB-231, MDA-MB-435S, MDA-MB-436, MDA-MB-468, T-47D, SK-BR-3, MDA-MB-453, ZR-75-1) were analyzed for DNA methylation of the CpG island in the promoter region of miR-34b/c using pyro-sequencing as above, methylation was observed in 15 of the gastric cancer cell lines (MKN1, MKN7, MKN74, SH101, SNU1, SNU638, JRST, KatoIII, AZ521, MKN28, MKN45, NUGC3, NUGC4, AGS, NCI-N87) (94%), 5 of the pancreatic cancer cell lines (BxPC-3, KLM-1, MIAPaCa, PK-8, PK-9) (56%), and 7 of the breast cancer cell lines (MCF7, MDA-MB-231, MDA-MB-435S, MDA-MB-468, T-47D, MDA-MB-453, ZR-75-1) (78%).

These results shows that DNA methylation of the CpG island in the promoter region of miR-34b/c was detected at high level in colorectal cancer cell and colon tumor tissue but hardly detected in normal tissue, revealing that the CpG island in the promoter region of miR-34b/c is specifically methylated in colorectal cancer, and suggesting that miR-34b/c gene undergoes silencing in colorectal cancer-specific manner. Also, the CpG island in the promoter region of miR-34b/c was methylated not only in colorectal cancer but also in gastric cancer, pancreatic cancer and breast cancer, suggesting that miR-34b/c gene may be being silenced.

Working Example 8

Functional Analysis of miR-34b/c

Based on the suggestion that miR-34b/c gene undergoes silencing in tumor cell-specific manner, we investigated on the possibility that miR-34b/c gene functions as tumor suppressor gene that suppresses expression of oncogene product. Firstly, in order to search for a gene whose expression is decreased by miR-34b/c expression, control miRNA (control miRNA (Ambion)), miR-34b (miR-34b precursor (Ambion)) and miR-34c (miR-34c precursor (Ambion)) were introduced into a HCT116 cell by electroporation, and after 48 hours RNA was extracted and subjected to microarray analysis. Also, for an intact HCT116 cell (mock) and a HCT116 cell treated with DNA methyltransferase inhibitor DAC (2 μM, 72 hours) (DAC), RNA extraction and microarray analysis were similarly carried out.

The results are shown in FIG. 13A. A comparison of the expression patterns of control miRNA (miRNA-control), miR-34b (miR-34b) and miR-34c (miR-34c) shows a group of genes whose expression was decreased by expressing miR-34b/c as indicated by a large case arc in top of FIG. 13A, which were considered to correspond to the target genes for miR-34b/c. Furthermore, a comparison between an intact HCT116 cell (mock) and a HCT116 cell with DAC treatment (DAC) and an analysis of genes that showed any difference revealed that the expression of many of the genes whose expression is decreased by expressing miR-34b/c was also decreased by DAC treatment. This is considered to be due to an increase in endogenous miR-34b/c expression by DAC treatment.

Then, in order to verify the microarray results, the expression of representative oncogenes MET (hepatocyte growth factor receptor) gene and MTB (v-myb myeloblastosis viral oncogene homolog) gene, cell-cycle associated genes CDK4 (cyclin-dependent kinase 4) gene and CCNE2 (Cyclin E2) gene, as well as SFRS2 (splicing factor, arginine/serine-rich 2) gene were analyzed by introducing control miRNA (control miRNA (Ambion)), miR-34b (miR-34b precursor (Ambion)) and miR-34c (miR-34c precursor (Ambion)) into HCT116 cells by electroporation, extracting RNA after 48 hours, analyzing by real-time RT-PCR using TaqMan Gene Expression Assay (Applied Biosystems). Also, RNA was extracted from an intact HCT116 cell (mock) and a HCT116 cell treated with DNA methyltransferase inhibitor DAC (2 µM, 72 hours) (DAC) and similarly analyzed. The result, as shown in FIG. 13B, indicates that mRNA expression levels of all of the foregoing genes were decreased by expressing miR-34b/c, as well as by treating with DAC.

Furthermore, for foregoing genes, changes in protein level were verified by western-blot analysis using an anti-MET antibody (MET), anti-CDK4 antibody (CDK4), anti-SFRS2 antibody (SFRS2), and anti-actin antibody as control (actin), as shown in FIG. 13C. It was shown that the expression levels of all of the aforementioned proteins (MET, CDK4 and SFRS2) were decreased by expressing miR-34b/c as well as by treating with DAC. It has been known that the effect of miRNA to inhibit the translation of RNA to a protein is more potent than its effect to degrade RNA. The result above also indicates a more marked decrease in protein level than in RNA level.

These results suggested that the oncogenes MET gene and MYB gene, cell-cycle associated genes CDK4 gene and Cyclin E2 gene, as well as SFRS2 gene are target genes for miR-34b/c. Furthermore, since the CpG island in the promoter region of miR-34b/c may undergo the silencing by specific methylation in tumor cell, resulting in suppression of miR-34b/c expression and increase in the expression of its target genes, miR-34b/c can be considered as a tumor suppressive miRNA, which functions in tumor-suppressive manner.

Numerous tumor suppressor genes and oncogenes have been identified so far whose transcription is suppressed by DNA methylation. Expression of these genes is restored by DNA methyltransferase inhibitor such as decitabine, drawing attention to DNA methyltransferase inhibitor as an effective cancer therapeutic. Current study by the inventors demonstrated a mechanism that DNA methyltransferase inhibitor restores the expression of miRNA that has a tumor suppressing effect, resulting in suppression of oncogene product expression, exhibiting a anti-cancer effect.

Working Example 9

Functional Analysis of BTG4

As shown in Working Example 4 above, the CpG island near miR-34b/c gene possesses a promoter activity in both directions, suggesting that BTG4 gene, which is transcribed in opposite direction to miR-34b/c, may also undergo a silencing in tumor cell. We therefore made an analysis on BTG4.

Firstly, BTG4 expression in 9 colorectal cancer cell lines (CaCO2, Colo320, DLD1, HCT116, HT29, LoVo, RKO, SW48 and SW480), DKO2 cell and human normal colon tissue, as well as BTG4 expression in the foregoing colorectal cancer cells treated with DAC (2 µM, 72 hours) were examined by RT-PCR using:

```
a forward primer:
5'-GTTTCTCTTTCTGATCTAGCAGGA-3'   (SEQ ID NO: 26)
and a reverse primer:
5'-TCAGAGTGCCAGTGACTTCTGTA-3'.   (SEQ ID NO: 27)
```

The results are shown in FIG. 14A.

As shown in the results in FIG. 14A, mRNA expression of BTG4 gene has been lost or at an extremely low level in all 9 colorectal cancer cell lines, but tends to markedly increased (restored) by DAC treatment. BTG4 gene was also expressed at a high level in the DKO2 cell. Thus, it is suggested that, in colorectal cancer cell, BTG4 gene is silenced and its expression is suppressed by DNA methylation of the CpG island in the promoter region of miR-34b/c.

The ability of BTG4 to propagating cells was then analyzed by colony-formation assay. A BTG4-expressing vector or control vector was introduced into colorectal cancer cell lines DLD1 cell and HCT116 cell. Transgenic cells were selected with the agent G418. The cells were fixed with methanol 10 to 14 days after gene transfer, stained with Giemsa staining, and colonies were counted. The results are shown in FIGS. 14B and 14C. FIG. 14C is a graphed result of FIG. 14B, indicating averages and standard deviations of three experimental results.

As understood by the results in FIGS. 14B and 14C, in the colorectal cancer cell transferred with the BTG4-expressing vector (BTG4), colony-forming ability has been decreased compared to the cell transferred with the control vector (vector). Thus, BTG4 was shown to have an effect to suppress tumor growth, implying a potential function of BTG4 gene as tumor suppressor gene.

Accordingly, the DNA methylation of the CpG island in the promoter region of miR-34b/c has been implicated in controlling not only transcription of miR-34b/c but also that of BTG4, showing a strong involvement in cellular canceration.

Working Example 10

DNA Methylation of miR-34b/c in Cases of Gastric Cancer

In the examples above, in colorectal cancer, it was suggested that the CpG island in the promoter region of miR-34b/c is specifically methylated in colorectal cancer cell and tissue. We further analyzed on DNA methylation of the same site in cases of gastric cancer.

For the cases of multiple gastric cancer, single gastric cancer and non-cancer, gastric vestibule mucosa was collected and DNA was extracted. DNA methylation of the CpG island in the promoter region of miR-34b/c was quantitatively analyzed by pyro-sequencing as in Working Example 7.

As shown in FIG. 15, DNA methylation level of miR-34b/c observed in background mucosa of gastric vestibule was 33.8% in average in the multiple gastric cancer cases (15 samples), 21.3% in average in the single gastric cancer cases (39 cases), and 22.3% in average in the non-cancer cases (46 samples). Thus, DNA methylation of miR-34b/c was observed in the multiple gastric cancer cases at significantly higher level compared to in the single gastric cancer and non-cancer cases, suggesting that it may be possible to detect a multiple gastric cancer case based on the level of DNA methylation of miR-34b/c in mucosa of gastric vestibule.

A similar experiment was carried out for mucosa of gastric corpus. As shown in FIG. 16, DNA methylation level of miR-34b/c observed in mucosa of gastric corpus was 21.6% in average in the multiple gastric cancer cases (15 samples), 19.1% in average in the single gastric cancer cases (39 cases) and 17.2% in average in the non-cancer cases (46 samples). Thus, DNA methylation of miR-34b/c was observed in the multiple gastric cancer cases at significantly higher level compared to in the single gastric cancer and non-cancer cases (p=0.045), suggesting that it may be possible to detect a multiple gastric cancer case based on the level of DNA methylation of miR-34b/c in mucosa of gastric corpus.

Furthermore, the average of DNA methylation levels of miR-34b/c in gastric vestibule and gastric corpus was, as shown in FIG. 17, 27.7% in average in the multiple gastric cancer cases, 19.9% in average in the single gastric cancer cases, and 19.6% in average in non-cancer cases. Thus, DNA methylation of miR-34b/c was observed in the multiple gastric cancer cases at significantly higher level compared to in the single gastric cancer and non-cancer cases (p<0.0001), suggesting that a multiple gastric cancer case may be detected at higher accuracy by employing the mean value of DNA methylation levels of miR-34b/c in mucosae of gastric vestibule and gastric corpus.

Also, these results reveals that the level of miR-34b/c DNA methylation shows a high value in multiple gastric cancer cases, suggesting the possibility that the detection of the level of miR-34b/c DNA methylation in gastric mucosa may be useful for predicting recurrence of gastric cancer. Furthermore, because a high level methylation is detected in some of the single cancer and non-cancer cases, it is suggested that a risk of carcinogenesis may be predicted based on the level of DNA methylation of miR-34b/c.

Working Example 11

DNA Methylation of miR-34b/c in Colorectal Cancer Cases

In the examples above, it was suggested that the CpG island in the promoter region of miR-34b/c is specifically methylated in colorectal cancer cell and tissue. We further analyzed the relation between DNA methylation of this site and the staging of colorectal cancer.

For colorectal adenoma (Adenoma) cases (12 samples), invasive cancer (Cancer) cases (18 samples), and severe atypical adenoma-intramucosal carcinoma (Sev-m) cases (5 samples), colon tissue (colonic biopsy) was collected, DNA was extracted, and DNA methylation of the CpG island in the promoter region of miR-34b/c was quantitatively analyzed by pyro-sequencing as in Working Example 7.

The result, as shown in FIG. 18, demonstrated that the level of DNA methylation of miR-34b/c in colonic biopsy tissue was at 22.9% in average in the colorectal adenoma (Adenoma) cases, 41.9% in average in the invasive cancer (Cancer) cases, and 34.8% in average in the severe atypical adenoma-intramucosal carcinoma (Sev-m) cases. Thus, DNA methylation of miR-34b/c was observed in invasive cancer cases at a significantly higher level compared to in colorectal adenoma cases (p=0.0011), suggesting that the staging of colorectal cancer can be predicted, and invasive cancer cases can be detected, based on the level of DNA methylation of miR-34b/c in colonic biopsy tissue.

Moreover, because it is often difficult to determine by magnified endoscopy examination whether a case revealing a type-IV Pit is a carcinoma or adenoma, we classified the cases with a type-IV Pit into 4b case (revealing a type-V Pit within the same lesion and being associated with a severe atypism, intra-adenomatous carcinoma or cancer) or IVb case (revealing a simple moderate adenoma), and then carried out a similar experiment as above to investigate DNA methylation level of miR-34b/c. The results, as shown in FIG. 19, were 44.5% in average in 4b cases (10 samples) and 22.4% in average in IVb cases (6 samples). Thus, even among type-IV Pit cases which cannot be distinguished by endoscopy, cases that are associated with cancer (4b) show a significantly higher level of DNA methylation for miR-34b/c compared to the cases that are not associated with cancer (IVb) (p=0.0028), suggesting the possibility that a risk of carcinogenesis can be predicted at high accuracy even in a case which is difficult to be diagnosed by endoscopy.

These results revealed that the level of DNA methylation of miR-34b/c is particularly high in the cases of invasive cancer among colorectal cancer, indicating that the prediction of the stage of colorectal cancer and the prediction of a risk of carcinogenesis can be enabled by detecting the level of DNA methylation of miR-34b/c using colonic (biopsy) tissue as sample.

As described above, the inventors have newly identified miR-34b/c as a miRNA that undergoes an epigenetic silencing by DNA methylation in a colorectal cancer cell. The inventors have further discovered for the first time, from detailed analysis of DNA methylation of the CpG island near miR-34b/c gene located in the chromosome 11q23.1, that said CpG island is the promoter of miR-34b/c gene and is directly involved in inactivation of miR-34b/c gene by being specifically methylated in various cancers such as colorectal cancer, gastric cancer, pancreatic cancer and breast cancer. The inventors have also revealed that a tumor suppressor gene product p53 induces the expression of miR-34b/c gene, and that miR-34b/c gene suppresses expression of cell-cycle regulatory genes such as Cyclin E2 gene and CDK4 gene as well as oncogenes such as MET gene and MYB gene, demonstrating that p53 functions as tumor suppressor gene product by indirectly controlling expression of oncogenes through miR-34b/c. Moreover, the inventors has discovered that the CpG island in the promoter region of miR-34b/c possesses a promoter activity for BTG4 gene, which is transcribed in opposite direction to miR-34b/c gene, and that BTG4 gene is also silenced by methylation of said CpG island in colorectal cancer cell. It has further been shown that BTG4 exhibits a suppressing effect on cancer cell proliferation, and thus BTG4 gene may function as a tumor suppressor gene.

These results demonstrated that, by the method of the present invention, or by using the kit of the present invention, a cancer, particularly colorectal cancer, gastric cancer, pancreatic cancer and breast cancer in a subject can easily and accurately be detected using a biological sample obtained from the subject. It is also suggested that the method of the present invention or the kit of the present invention is extremely useful not only for detecting a cancer, but also for predicting the stage of a cancer, for predicting a risk of carcinogenesis, and for predicting a risk of recurrence. The aforementioned CpG island directly controls the expression of two genes miR-34b/c gene and BTG4 gene whose expression is decreased in tumor tissue-specific manner in cancer cell as described above. Therefore, the method of the present invention, which detects a cancer based on the methylation of this region, is considered to be highly accurate.

Moreover, since the cancer therapeutic agent of the present invention increases the expression of miR-34b/c or BTG4 that functions like a tumor suppressor gene product in cancers such as colorectal cancer, gastric cancer, pancreatic cancer and breast cancer, it has been suggested to be capable of effectively suppressing the proliferation of cancer cells.

INDUSTRIAL APPLICABILITY

The expression of miR-34b/c gene is specifically suppressed in cancers such as colorectal cancer, gastric cancer, pancreatic cancer and breast cancer. According to the present invention, a method of detecting a cancer comprising detecting DNA methylation in a CpG island in a promoter region of miR-34b/c gene, and a kit for detecting a cancer based on such method can be provided. Accordingly, the present invention would greatly contribute to diagnosing, treating and researching cancers such as colorectal cancer, gastric cancer, pancreatic cancer and breast cancer.

Also, since expression of miR-34b and/or miR-34c is specifically decreased in a cancer cell and they have a suppressing effect on oncogene expression, a therapeutic agent for cancer comprising miR-34b and/or miR-34c or a nucleic acid encoding miR-34b and/or miR-34c gene can be provided. Such cancer therapeutic agent can be expected to be applied for a pharmaceutical product which exhibits a high therapeutic effect. Furthermore, since the expression of BTG4 is specifically decreased in cancer cell, and it has a suppressing effect on cell proliferation, a therapeutic agent for cancer comprising BTG4 or a nucleic acid encoding BTG4 gene can be provided. Such cancer therapeutic agent can be expected to be applied for a pharmaceutical product which exhibits a high therapeutic effect.

BRIEF DESCRIPTION OF THE DRAWINGS

FIG. 9C is a diagram showing the result of an analysis of DNA methylation of the CpG island near miR-34b/c gene in 126 clinical samples of colorectal cancer.

FIG. 19 is a diagram showing the results of a pyro-sequencing analysis of DNA methylation of the CpG island near miR-34b/c gene in DNA samples collected from colorectal cancer cases with type-IV Pit, wherein the cases are classified into 4b cases (cases revealing type-V Pit within the same lesion, and being associated with severe atypism, intra-adenomatous carcinoma or cancer) and IVb cases (revealing simple moderate adenoma).

Figure 1:
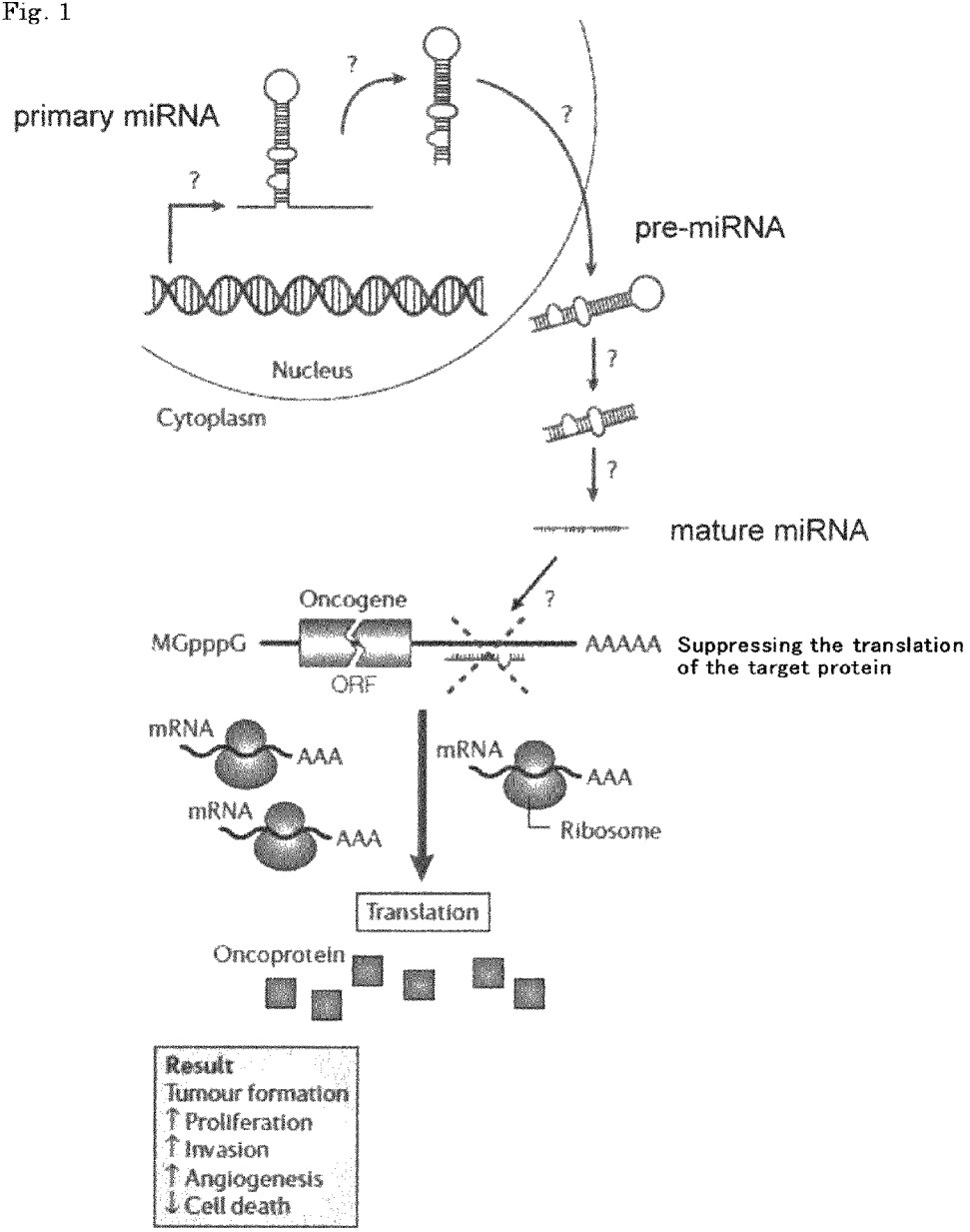
FIG. 1 is a schematic diagram showing functions of a microRNA.
Figure 2:
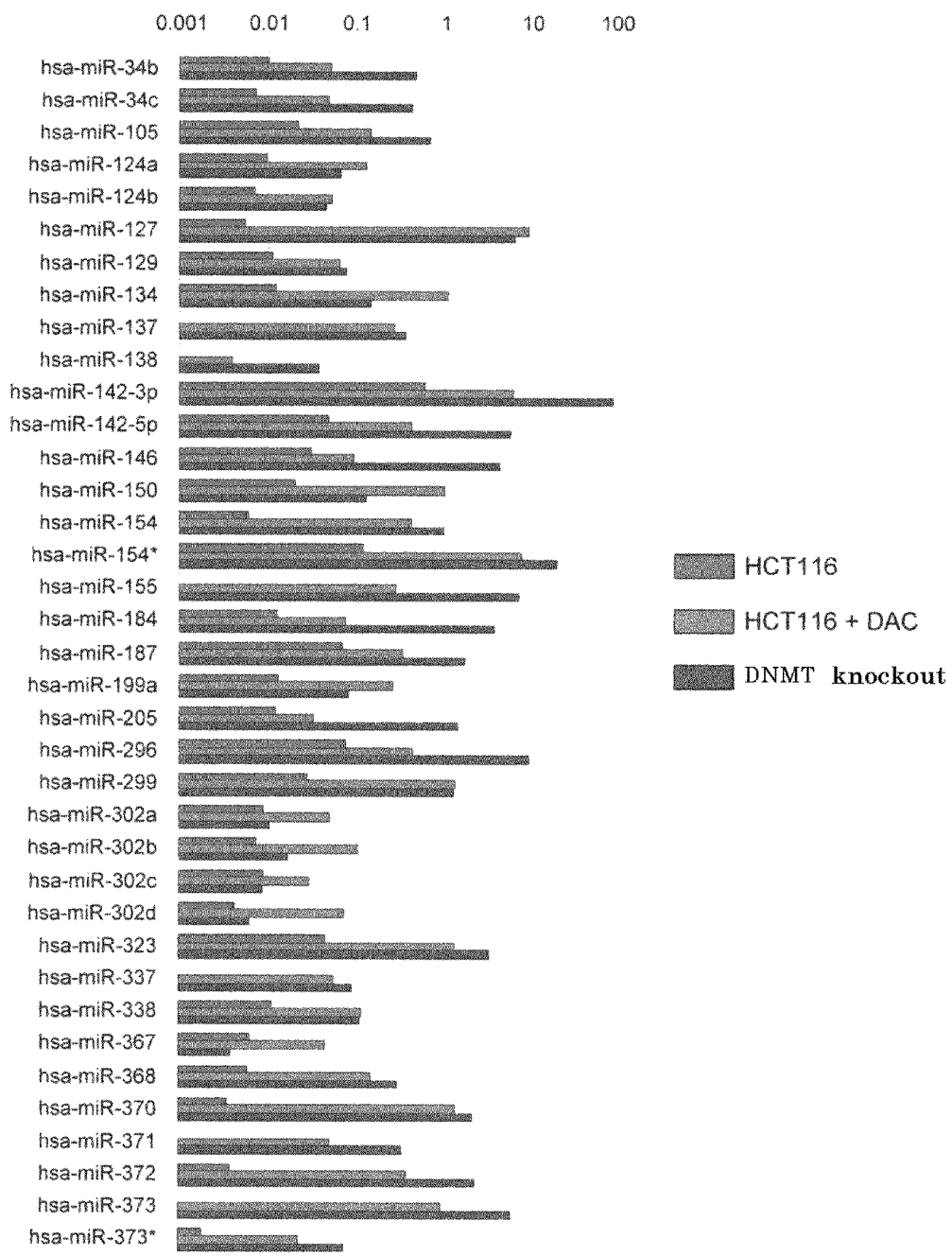
FIG. 2 is a diagram showing the results of an analysis of 37 miRNA in a colorectal cancer cell line HCT116 (HCT116), a HCT116 cell treated with DNA methyltransferase inhibitor (HCT116+DAC), and a HCT116 cell in which DNA methyltransferase gene has been knocked out (DNMT knockout).
Figure 3A:
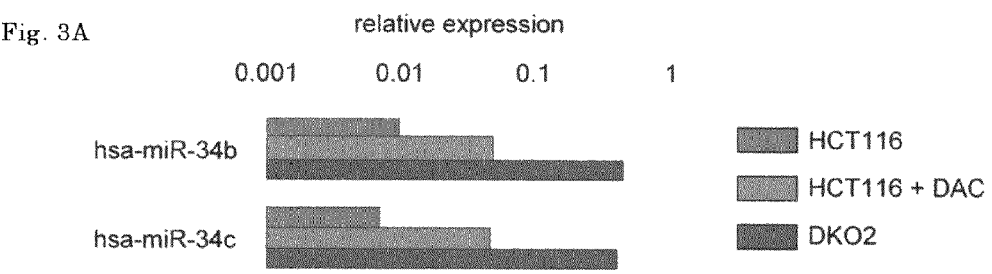
FIG. 3A is a diagram showing the expression level of hsa-miR-34b and hsa-miR-34c in a colorectal cancer cell line HCT116 (HCT116), a HCT116 cell treated with DNA methyltransferase inhibitor (HCT116+DAC), and a HCT116 cell in which DNA methyltransferase gene has been knocked out (DKO2).
Figure 3B:
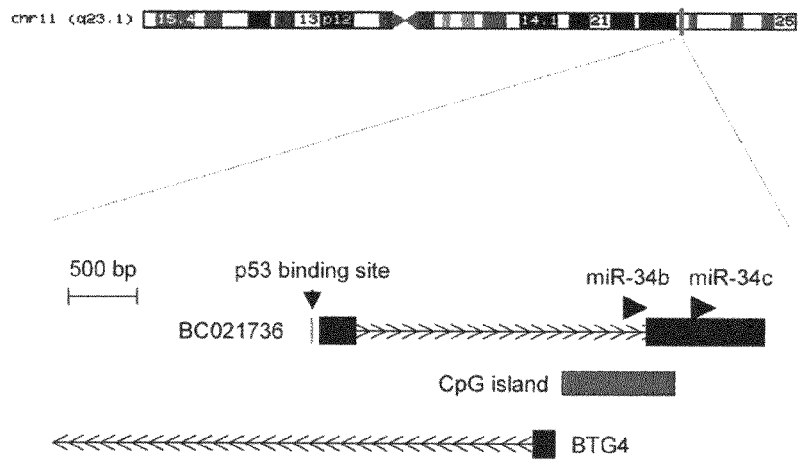
FIG. 3B is a schematic diagram showing the sequence near miR-34b/c gene in chromosome 11q23.1.
Figure 4A:
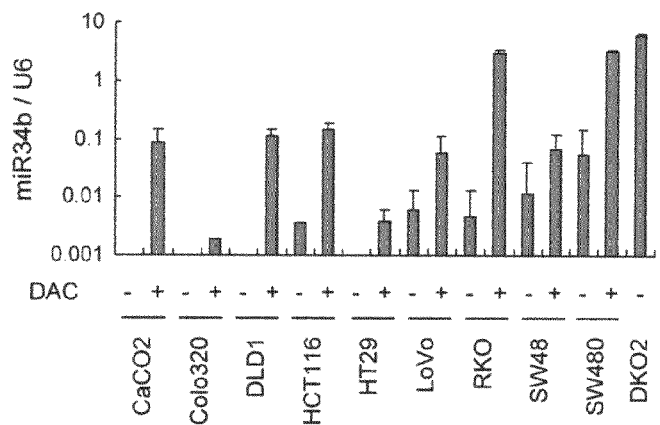
FIG. 4A is a diagram showing the expression level of miR-34b in 9 colorectal cancer cell lines (CaCo2, Colo320, DLD1, HCT116, HT29, LoVo, RKO, SW48, SW480), and said cell lines treated with DAC, as well as a HCT116 cell in which DNA methyltransferase has been knocked out (DKO2) as control.
Figure 4B:
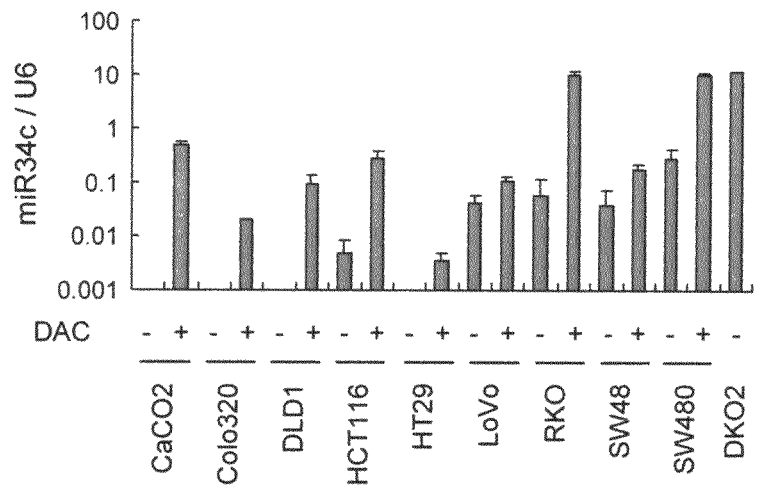
FIG. 4B is a diagram showing the expression level of miR-34c in 9 colorectal cancer cell lines (CaCo2, Colo320, DLD1, HCT116, HT29, LoVo, RKO, SW48, SW480), and said cell lines treated with DAC, as well as a HCT116 cell in which DNA methyltransferase has been knocked out (DKO2) as control.
Figure 5A:
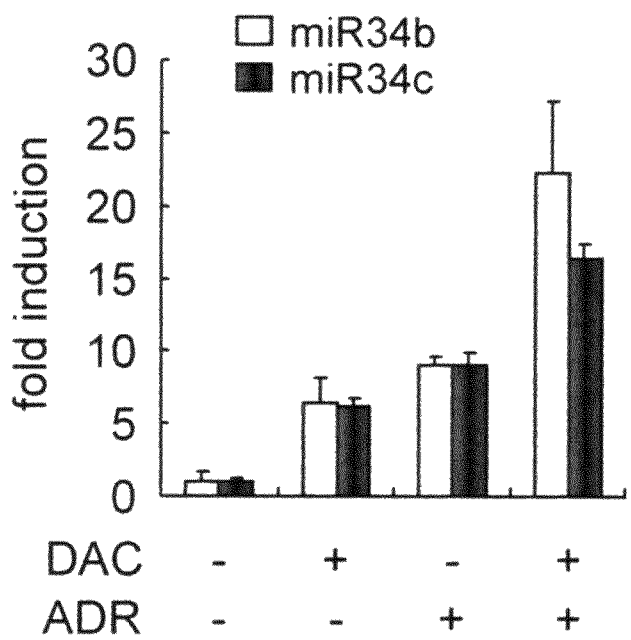
FIG. 5A is a diagram showing the expression levels of miR-34b and miR-34c, in a HCT116 cell without treatment, with DAC treatment, with ADR treatment, and with both DAC treatment and ADR treatment.
Figure 5B:
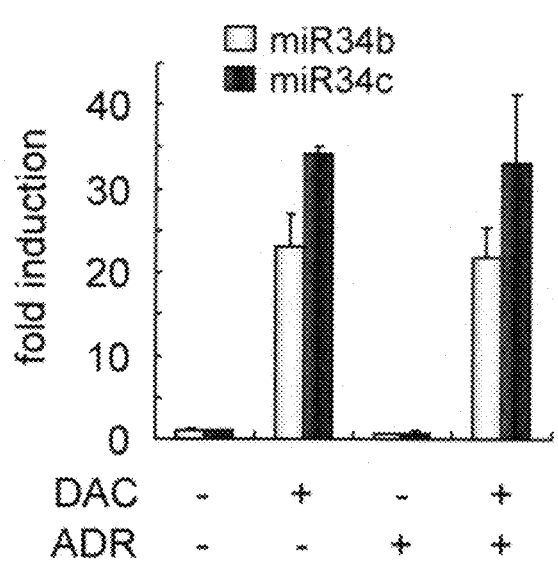
FIG. 5B is a diagram showing the expression levels of miR-34b and miR-34c, in p53 gene-knockout HCT116 cell without treatment, with DAC treatment, with ADR treatment, and with both DAC treatment and ADR treatment.
Figure 5C:
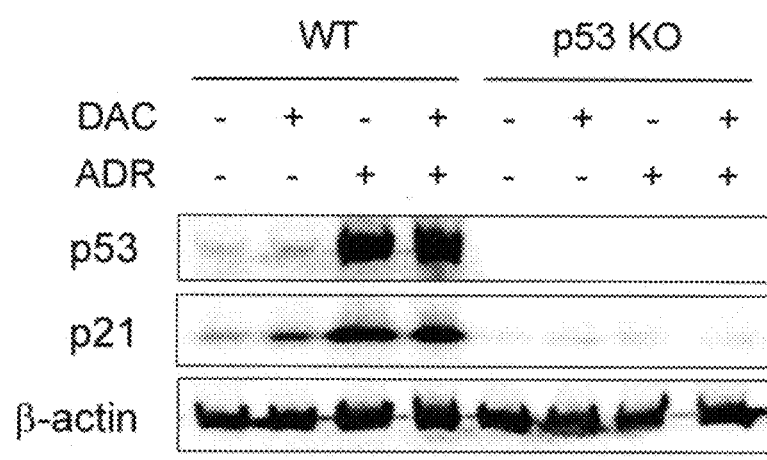
FIG. 5C is a diagram showing the protein expression levels of p53, p21 and β-actin, in a HCT116 cell (WT) and in p53 gene-knockout HCT116 cell (p53KO), each without treatment, with DAC treatment, with ADR treatment, and with both DAC treatment and ADR treatment.
Figure 6A:
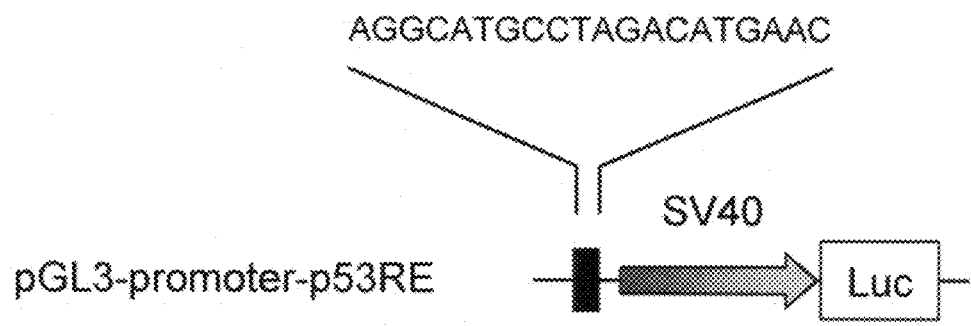
FIG. 6A is a schematic diagram showing a vector pGL3-promoter-p53RE in which a p53-binding sequence that is located near miR-34b/c has been inserted into pGL3-promoter, a luciferase vector with SV40 promoter.
Figure 6B:
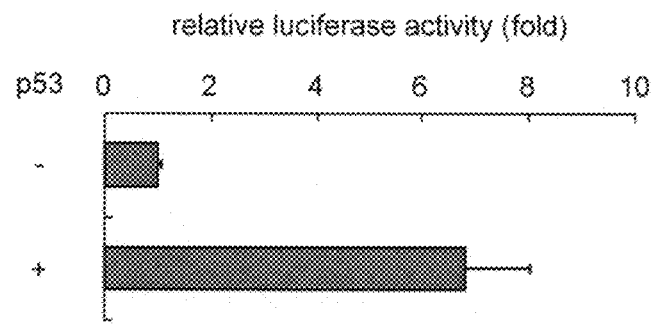
FIG. 6B is a diagram showing luciferase activity of pGL3-promoter-p53RE, being introduced into a HCT116 cell either concurrently with a control expression vector, or concurrently with p53-expressing vector.
Figure 7:
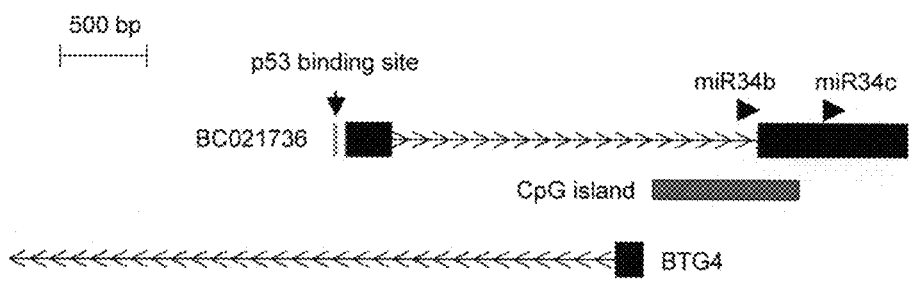
FIG. 7 is a diagram showing a schematic diagram showing the sequence near miR-34b/c gene (top), and a graph showing the relation between the sequence near miR-34b/c gene and the trimethylation of the fourth lysine of histone H3 (H3-K4) (bottom).
Figure 7:
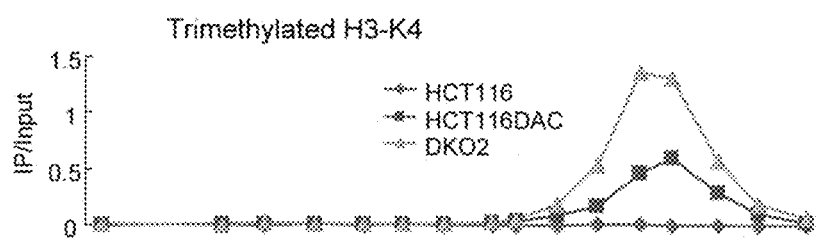
Figure 8A:
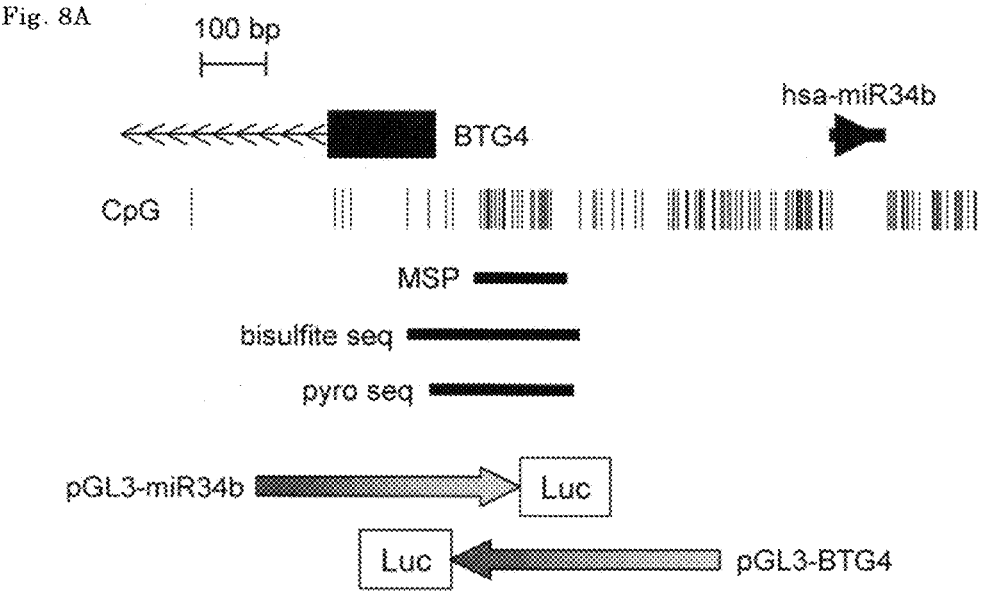
FIG. 8A is a schematic diagram showing the CpG island near miR-34b/c gene.
Figure 8B:
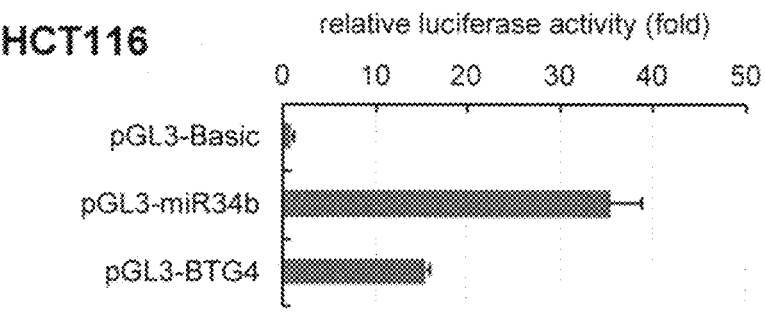
FIG. 8B is a schematic diagram showing the results of measuring luciferase activity of colorectal cancer cell lines HCT116 and DLD1 transferred with a control luciferase vector (pGL3-Basic) or a luciferase vector in which the promoter region near miR-34b/c gene has been inserted (pGL3-miR-34b/c or pGL3-BTG4).
Figure 8B:
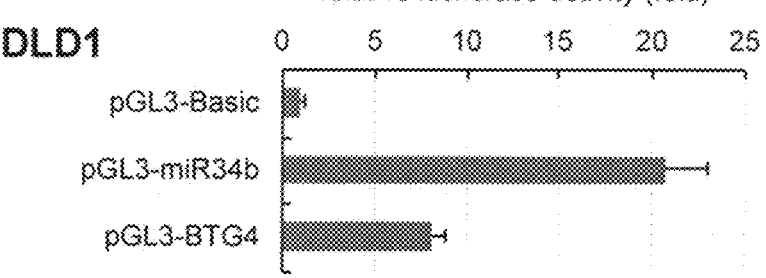
Figure 9A:
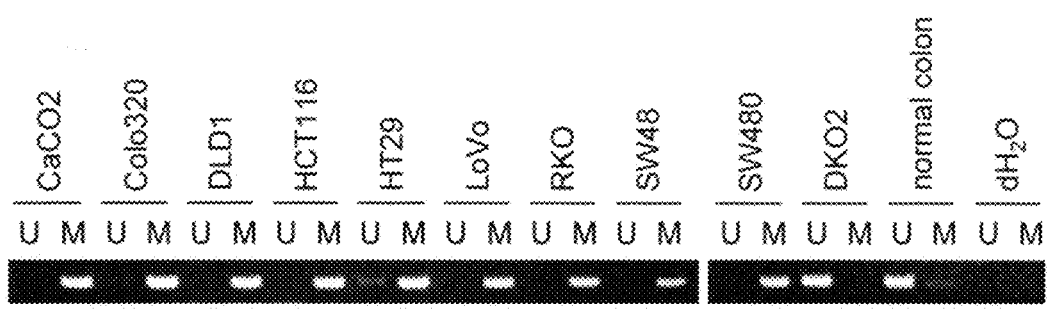
FIG. 9A is a diagram showing the results of an analysis by methylation-specific PCR of DNA methylation of the CpG island near miR-34b/c gene in colorectal cancer cell lines (CaCo2, Colo320, DLD1, HCT116, HT29, LoVo, RKO, SW48, SW480) and in a HCT116 cell in which DNA methyltransferase has been knocked out (DKO2).
Figure 9B:
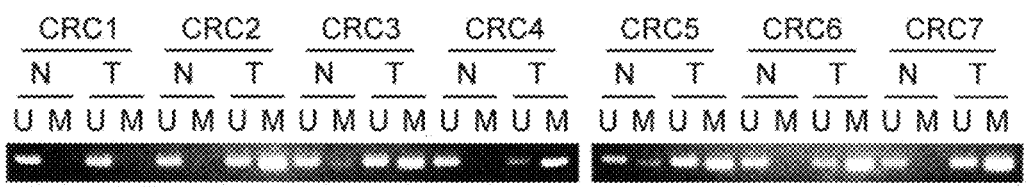
FIG. 9B is a diagram showing the result of an analysis by methylation-specific PCR of DNA methylation of the CpG island near miR-34b/c gene in tumor tissue (T) and non-tumor tissue (T) of 7 clinical samples of colorectal cancer.
Figure 10:
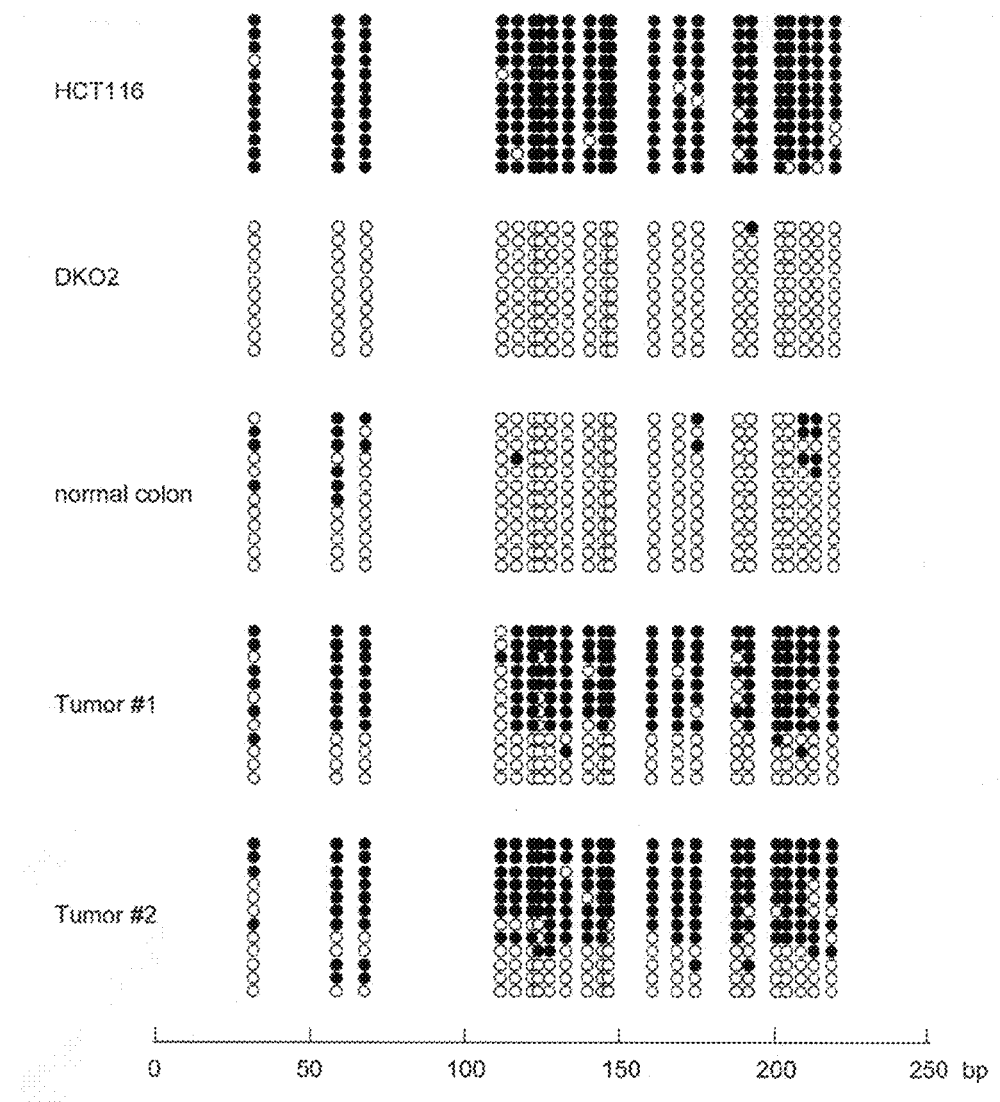
FIG. 10 is a diagram showing the result of an analysis by bisulfite sequencing of DNA methylation of the CpG island near miR-34b/c gene in a HCT116 cell (HCT116), DKO2 cell (DKO2), normal colon tissue (normal colon), and 2 colon tumor tissue samples (Tumor#1 and Tumor#2).
Figure 11:
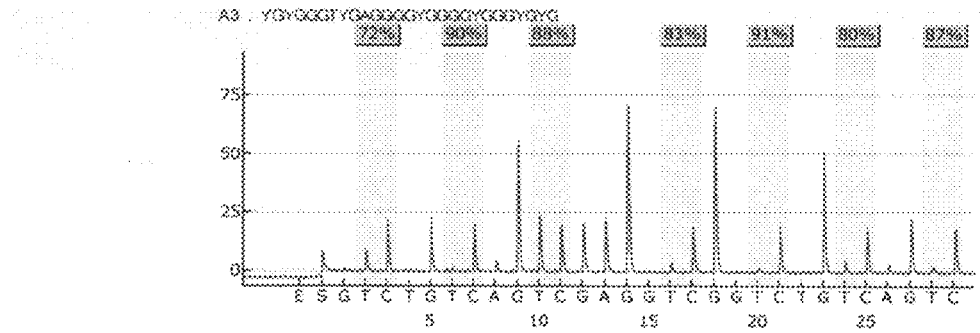
FIG. 11 is a diagram showing the result of an analysis by pyro-sequencing of DNA methylation of the CpG island near miR-34b/c gene in a HCT116 cell (HCT116), DKO2 cell (DKO2), normal colon tissue (normal colon), and colon tumor tissue (Tumor#1).
Figure 11:
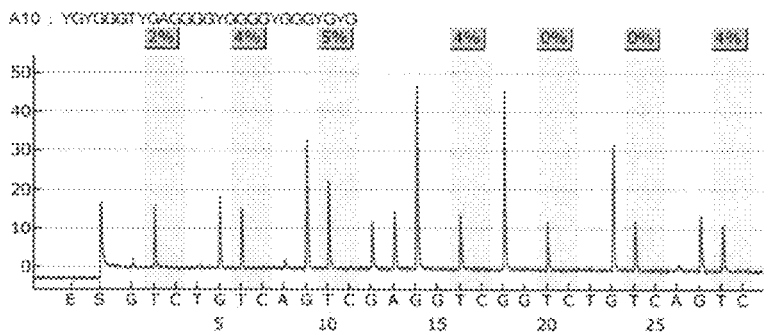
Figure 11:
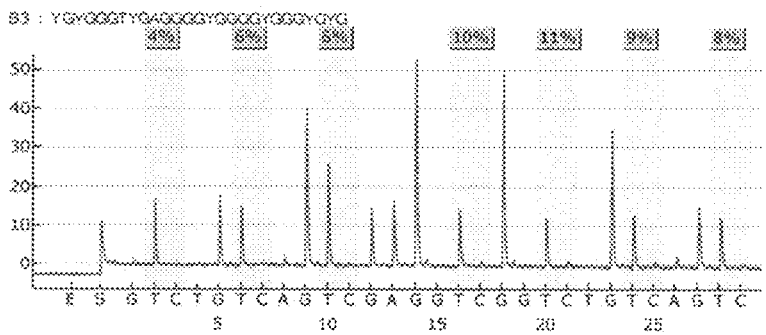
Figure 11:
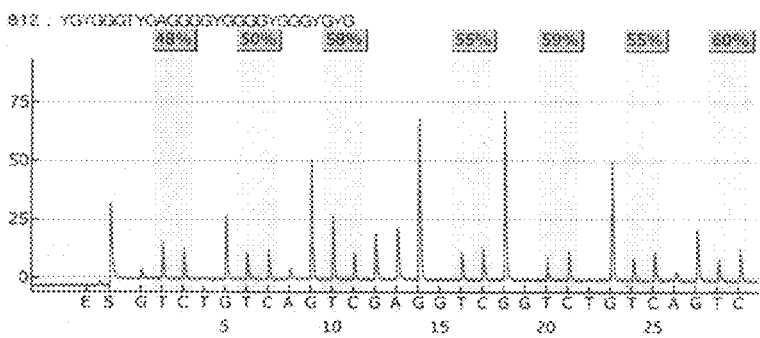
Figure 12:
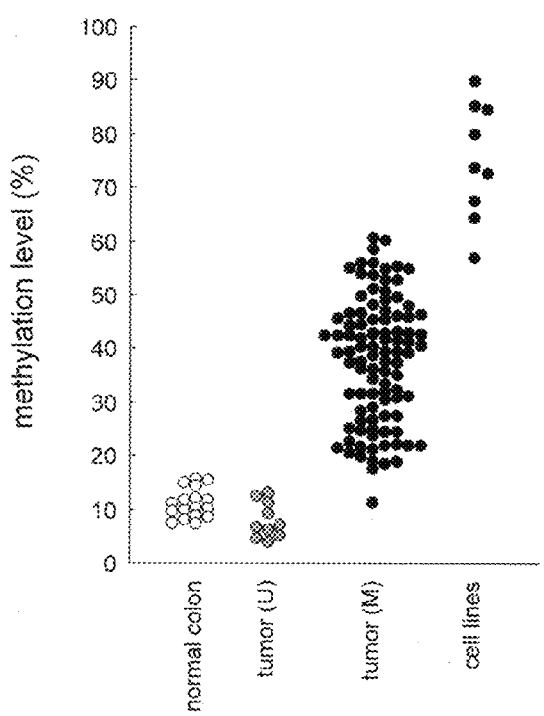
FIG. 12 is a diagram showing the result of an analysis by pyro-sequencing of DNA methylation of the CpG island near miR-34b/c gene in normal colon tissue (n=17) (normal colon), in colon tumor tissue determined to be methylation-negative by MSP (n=10) (tumor(U)), in colon tumor tissue determined to be methylation-positive by MSP (n=101) (tumor(M)), and in colorectal cancer cell lines (n=9) (cell lines).
Figure 13A:
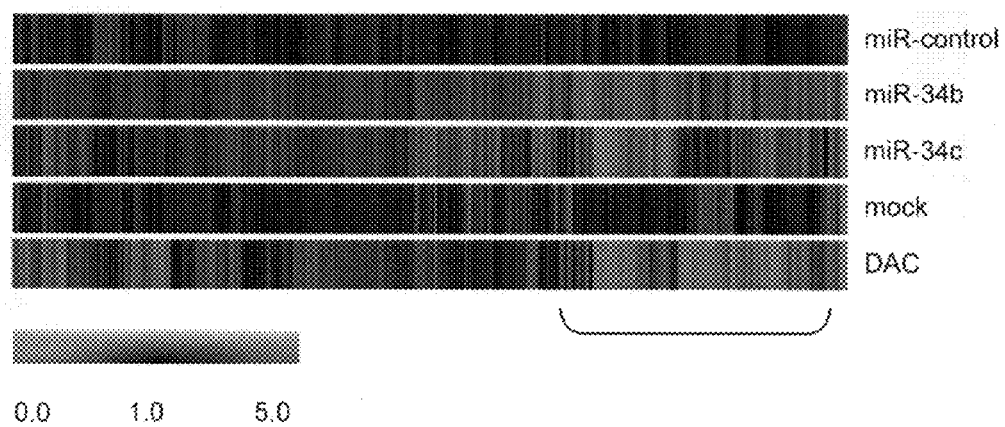
FIG. 13A is a diagram showing the result of a microarray analysis for a HCT116 cell transferred with a control miRNA (miR-control), miR-34b (miR-34b) or miR-34c (miR-34c), or a HCT116 cell without treatment (mock), or a HCT116 cell with DAC treatment (DAC).
Figure 13B:
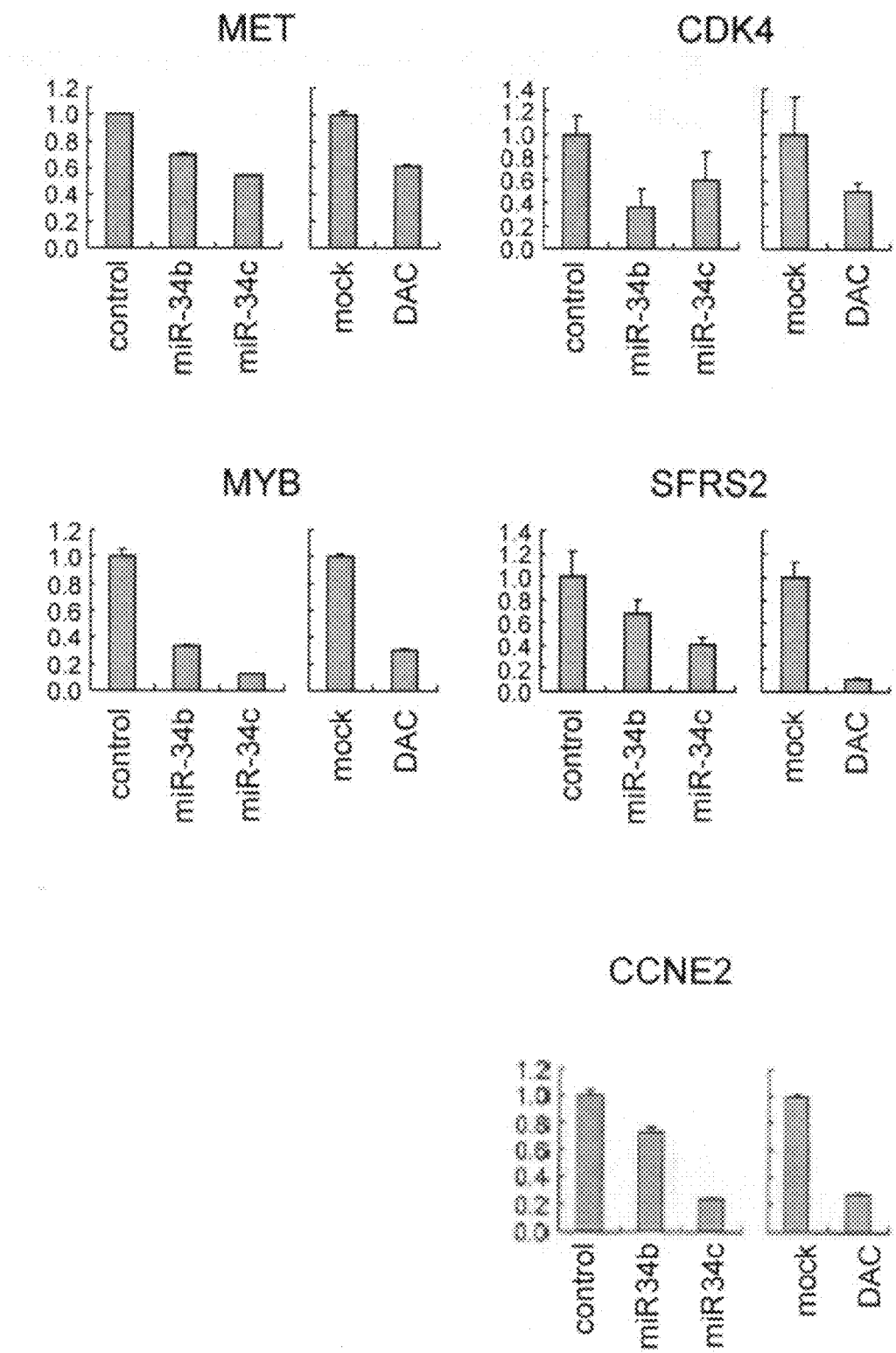
FIG. 13B is a diagram showing the result of a realtime PCR analysis of the expression of oncogenes MET gene and MYB gene, cell-cycle genes CDK4 gene and CCNE2 gene, and SFRS2 gene for a HCT116 cell transferred with a control miRNA (miR-control), miR-34b (miR-34b) or miR-34c (miR-34c), or a HCT116 cell without treatment (mock), or a HCT116 cell with DAC treatment (DAC).
Figure 13C:
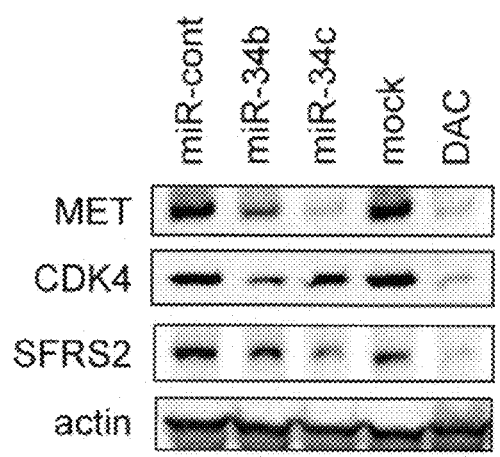
FIG. 13C is a diagram showing the result of an western-blot analysis of protein expression of a oncogene product MET, a cell-cycle gene product CDK4, and SFRS2 for a HCT116 cell transferred with control miRNA (miR-control), miR-34b (miR-34b) or miR-34c (miR-34c), or a HCT116 cell without treatment (mock), or a HCT116 cell with DAC treatment (DAC).
Figure 14A:
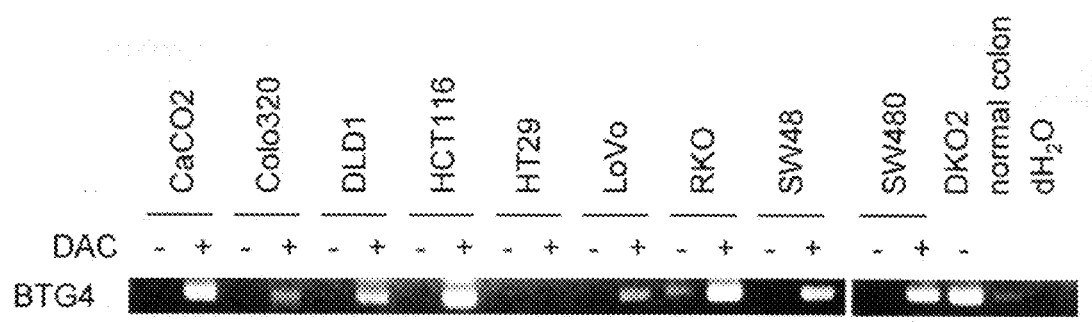
FIG. 14A is a diagram showing the expression level of BTG4 gene in 9 colorectal cancer cell lines (CaCo2, Colo320, DLD1, HCT116, HT29, LoVo, RKO, SW48, SW480) and said cell lines treated with DAC, as well as in DKO2 cell (DKO2) and normal colon tissue (normal colon).
Figure 14B:
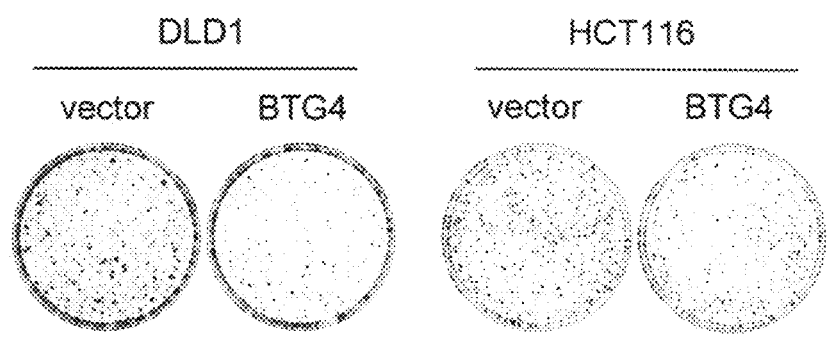
FIG. 14B is a diagram showing the results of a colony-formation assay in a DLD1 cell or HCT116 cell transferred with a control vector (vector) or BTG4-expressing vector (BTG4).
Figure 14C:
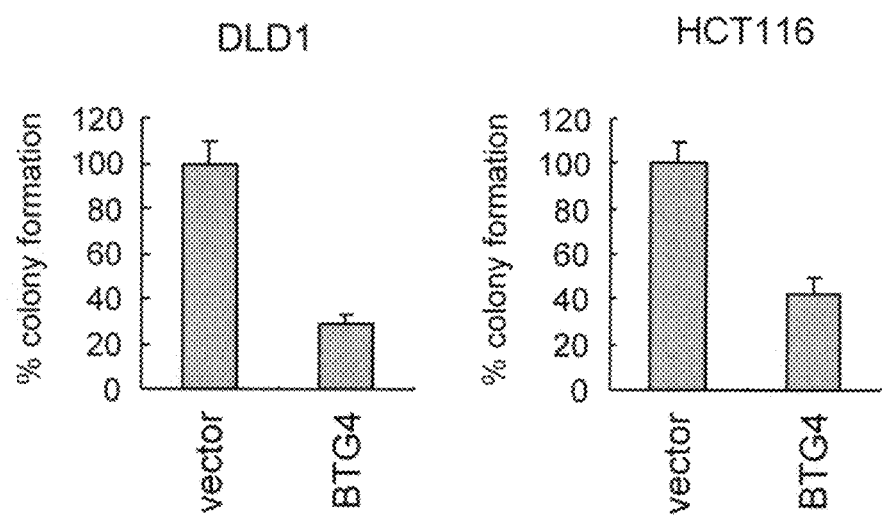
FIG. 14C is a graph showing the results of a colony-formation assay in a DLD1 cell or HCT116 cell transferred with a control vector (vector) or BTG4-expressing vector (BTG4).
Figure 15:
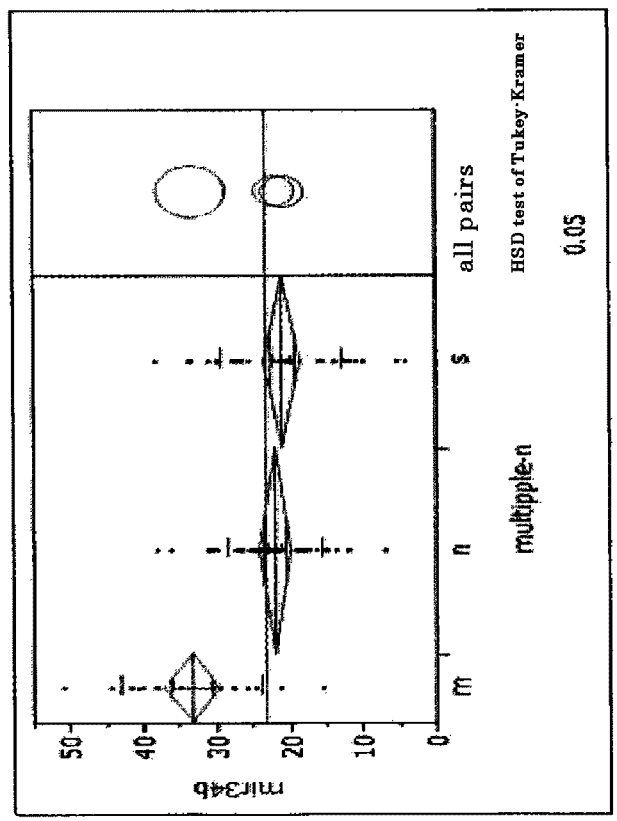
FIG. 15 is a diagram showing the result of a pyro-sequencing analysis of DNA methylation of the CpG island near miR-34b/c gene in gastric vestibule mucosa in multiple cases of gastric cancer, single cases of gastric cancer, or non-cancer cases.
Figure 16:
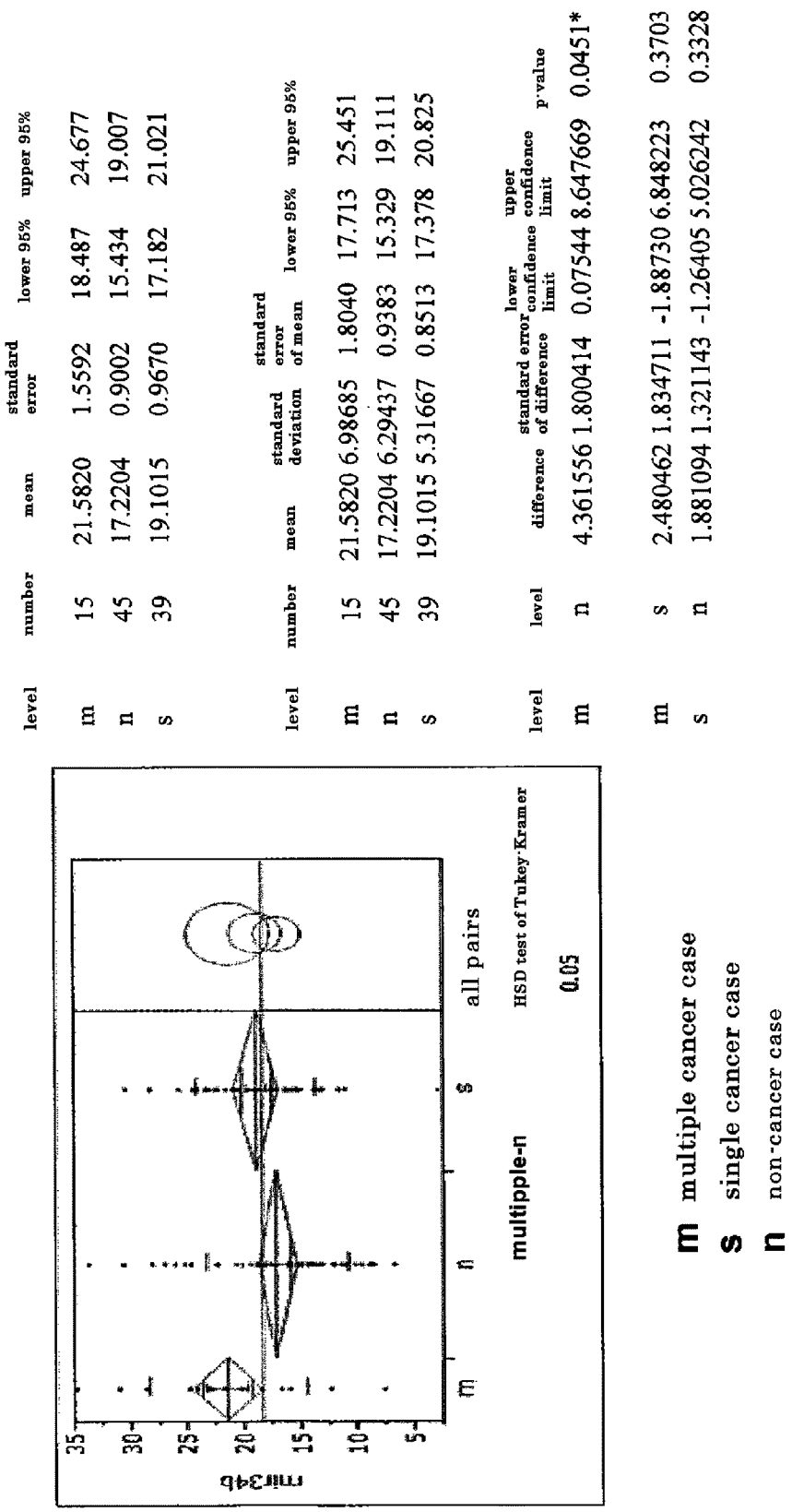
FIG. 16 is a diagram showing the result of a pyro-sequencing analysis of DNA methylation of the CpG island near miR-34b/c gene in gastric corpus mucosa in multiple cases of gastric cancer, single cases of gastric cancer, or non-cancer cases.
Figure 17:
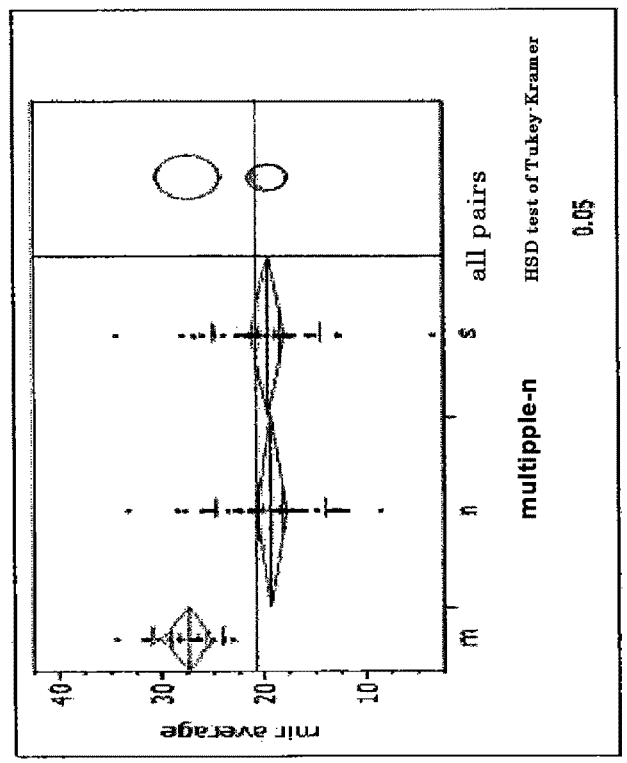
FIG. 17 is a diagram showing the averages of the results of a pyro-sequencing analysis of DNA methylation of the CpG island near miR-34b/c gene in gastric vestibule mucosa and gastric corpus mucosa in multiple cases of gastric cancer, single cases of gastric cancer, or non-cancer cases.
Figure 18:
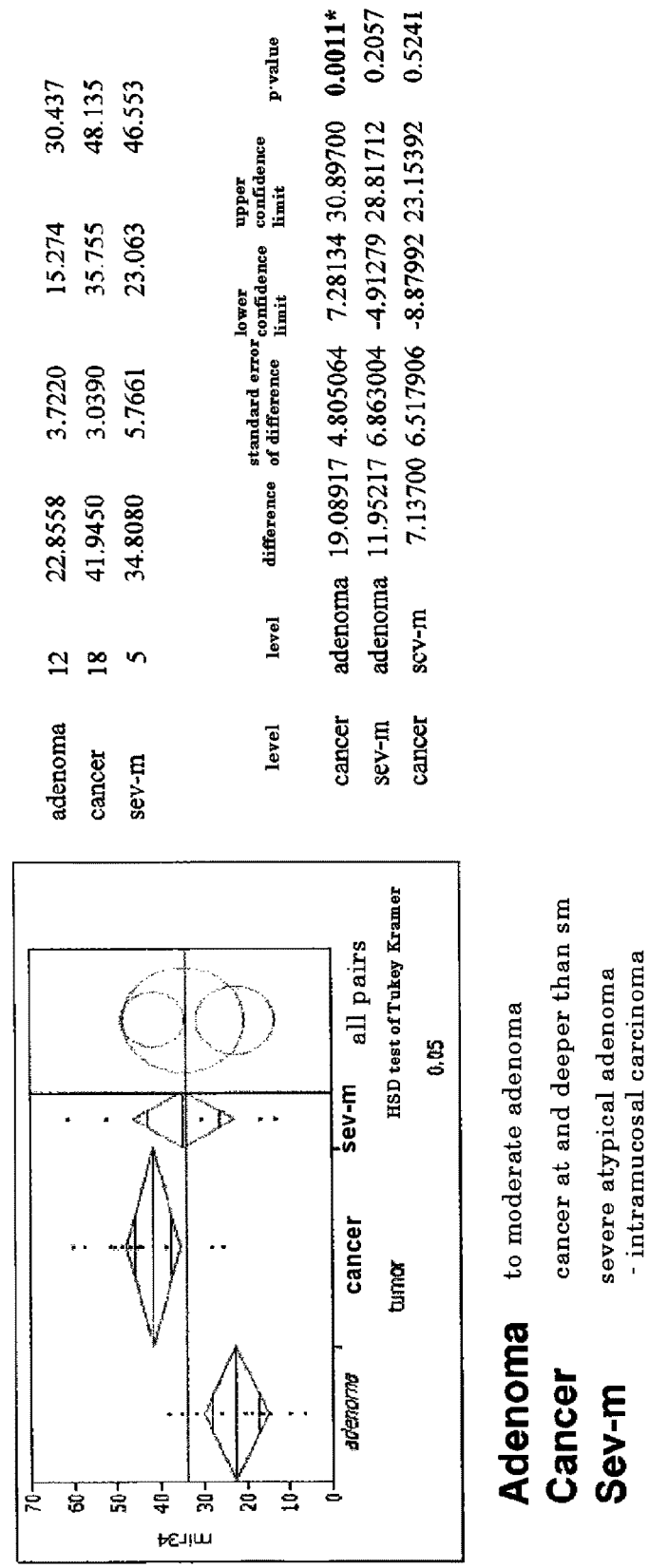
FIG. 18 is a diagram showing the results of a pyro-sequencing analysis of DNA methylation of the CpG island near miR-34b/c gene in biopsy tissue collected from the cases of colorectal cancer (Adenoma: up to moderate adenoma, Cancer: (invasive) cancer at or deeper than sm, Sev-m: severe atypical adenoma-intramucosal carcinoma) cases.

The invention claimed is:

1. A method for treating a cancer in a subject comprising:
   detecting in a biological sample obtained from the subject a methylated CpG in a CpG island in a promoter region of a microRNA34b gene and/or a microRNA34c gene, and when the methylated CpG is detected, then
   administering to the subject in need thereof an agent comprising an isolated nucleic acid encoding the microRNA34b gene and/or the microRNA34c gene, or an isolated microRNA34b and/or an isolated microRNA34c.

2. The method according to claim 1, wherein the cancer is selected from the group consisting of colorectal cancer, gastric cancer, pancreatic cancer and breast cancer.

3. The method according to claim 1, wherein the cancer is selected from the group consisting of colorectal cancer and gastric cancer.

4. The method according to claim 1, wherein the cancer is selected from the group consisting of invasive colorectal cancer and multiple gastric cancer.

5. The method according to claim 1, wherein the nucleic acid encoding the microRNA34b gene is encoding a polynucleotide sequence that is identical to or substantially identical to a polynucleotide sequence of SEQ ID NO:1, and the nucleic acid encoding the microRNA34c gene is encoding a polynucleotide sequence that is identical to or substantially identical to a polynucleotide sequence of SEQ ID NO:3.

6. The method according to claim 1, wherein the microRNA34b has a polynucleotide sequence that is identical to or substantially identical to a polynucleotide sequence of SEQ ID NO:2, and the microRNA34c has a polynucleotide sequence that is identical to or substantially identical to a polynucleotide sequence of SEQ ID NO:4.

7. A method for treating a cancer in a subject comprising: administering to the subject in need thereof an agent comprising an isolated nucleic acid encoding a microRNA34b gene and/or a microRNA34c gene, or an isolated microRNA34b and/or an isolated microRNA34c, wherein the subject has been determined to have a methylated CpG in a CpG island in a promoter region of a microRNA34b gene and/or a microRNA34c gene.

8. The method according to claim 7, wherein the cancer is selected from the group consisting of colorectal cancer, gastric cancer, pancreatic cancer and breast cancer.

9. The method according to claim 7, wherein the cancer is selected from the group consisting of colorectal cancer and gastric cancer.

10. The method according to claim 7, wherein the cancer is selected from the group consisting of invasive colorectal cancer and multiple gastric cancer.

11. The method according to claim 7, wherein the nucleic acid encoding the microRNA34b gene is encoding a polynucleotide sequence that is identical to or substantially identical to a polynucleotide sequence of SEQ ID NO:1, and the nucleic acid encoding the microRNA34c gene is encoding a polynucleotide sequence that is identical to or substantially identical to a polynucleotide sequence of SEQ ID NO:3.

12. The method according to claim 7, wherein the microRNA34b has a polynucleotide sequence that is identical to or substantially identical to a polynucleotide sequence of SEQ ID NO:2, and the microRNA34c has a polynucleotide sequence that is identical to or substantially identical to a polynucleotide sequence of SEQ ID NO:4.

13. A method for treating a cancer in a subject comprising: administering to the subject in need thereof an agent comprising an isolated nucleic acid encoding a microRNA34b gene and/or a microRNA34c gene, or an isolated microRNA34b and/or an isolated microRNA34c, wherein a CpG island in a promoter region of a microRNA34b gene and/or a microRNA34c gene of said cancer has been determined to be methylated.

14. The method according to claim 13, wherein the cancer is selected from the group consisting of colorectal cancer, gastric cancer, pancreatic cancer and breast cancer.

15. The method according to claim 13, wherein the cancer is selected from the group consisting of colorectal cancer and gastric cancer.

16. The method according to claim 13, wherein the cancer is selected from the group consisting of invasive colorectal cancer and multiple gastric cancer.

17. The method according to claim 13, wherein the nucleic acid encoding the microRNA34b gene is encoding a polynucleotide sequence that is identical to or substantially identical to a polynucleotide sequence of SEQ ID NO:1, and the nucleic acid encoding the microRNA34c gene is encoding a polynucleotide sequence that is identical to or substantially identical to a polynucleotide sequence of SEQ ID NO:3.

18. The method according to claim 13, wherein the microRNA34b has a polynucleotide sequence that is identical to or substantially identical to a polynucleotide sequence of SEQ ID NO:2, and the microRNA34c has a polynucleotide sequence that is identical to or substantially identical to a polynucleotide sequence of SEQ ID NO:4.

* * * * *

```
                        SEQUENCE LISTING

<160> NUMBER OF SEQ ID NOS: 27

<210> SEQ ID NO 1
<211> LENGTH: 84
<212> TYPE: DNA
<213> ORGANISM: human

<400> SEQUENCE: 1
gtgctcggtt tgtaggcagt gtcattagct gattgtactg tggtggttac aatcactaac      60
tccactgcca tcaaaacaag gcac                                            84

<210> SEQ ID NO 2
<211> LENGTH: 23
<212> TYPE: RNA
<213> ORGANISM: human

<400> SEQUENCE: 2
uaggcagugu cauuagcuga uug                                             23

<210> SEQ ID NO 3
<211> LENGTH: 77
<212> TYPE: DNA
<213> ORGANISM: human

<400> SEQUENCE: 3
agtctagtta ctaggcagtg tagttagctg attgctaata gtaccaatca ctaaccacac      60
ggccaggtaa aaagatt                                                    77

<210> SEQ ID NO 4
<211> LENGTH: 23
<212> TYPE: RNA
<213> ORGANISM: human

<400> SEQUENCE: 4
aggcagugua guuagcugau ugc                                             23

<210> SEQ ID NO 5
<211> LENGTH: 978
<212> TYPE: DNA
<213> ORGANISM: human
```

<400> SEQUENCE: 5

```
cgctttccca gggcggaatg gtcacggaaa ctgggtaggc tgggggcctt cttgggaat       60 gagggagtgg aggagctctt tgtccctcct gctagatcag aaagagaaac gtctcaagaa      120
tctgggcctc catcttctag gcgtctccct tggaggccct tcaggaccg cccacagcgc      180 tttctctcag cctcctcccc cccccatcc cctcccccac ccgcccgtc tcgcgcccgc       240 cccgcccctc ggcccgcggg gttccaagga cggttggtcg ccccgccac agtcactcgg     300 ccgctcagag cggcggggcg cacggggtcg agagagccag ctctagggtt tggggctggg    360
aactgaagcc tggcgtgaag gaagtgggag cccgggccga ggaggcgaag gggaaaggaa    420
aagcgagggg aacctgagcg ggagggccct gagaggagcg ggaggctgcg ggaaggggag    480
gcctggcact cctgggggtc atggggtcg gggcgcggct cccggcctgg gagggcgcgg    540
gtcctccccg gcagcgccgc ccgctggccc agctacgcgt gttgtgcgct gcgaggccgg    600
cgggggtccc gctgggcccg ggggtgtcct cgggggccgc ttgcgcccag ccatggtagg    660 gcgtccccg gtgaaatggg gtccgaggcg ggccccgacc ccgcgtcggc gctgcggacc     720
gtccgggagc tgcagccgcg ggtgcccggt gctcggtttg taggcagtgt cattagctga   780
ttgtactgtg gtggttacaa tcactaactc cactgccatc aaaacaaggc acagcatcac   840
cgccgcccgg ccgggaagaa gacgccggct cgggcagccc gcagccttcg agagaagatg   900
cctgagaagc gcggcgtcgg cgtgggtcct gcgcagcctg ccccgcgagc gcccgctgca   960
agtgcgagga aacccgcg                                                  978
```

```
<210> SEQ ID NO 6
<211> LENGTH: 262
<212> TYPE: DNA
<213> ORGANISM: human
```

<400> SEQUENCE: 6

```
gtctcaagaa tctgggcctc catcttctag gcgtctccct tggaggccct tcaggaccg      60 cccacagcgc tttctctcag cctcctcccc cccccatcc cctcccccac ccgcccgtc      120 tcgcgcccgc cccgcccctc ggcccgcggg gttccaagga cggttggtcg ccccgccac    180 agtcactcgg ccgctcagag cggcggggcg cacggggtcg agagagccag ctctagggtt   240
tggggctggg aactgaagcc tg                                             262
```

```
<210> SEQ ID NO 7
<211> LENGTH: 223
<212> TYPE: DNA
<213> ORGANISM: human
```

<400> SEQUENCE: 7

```
tctcccttgg aggcccttca gggaccgccc acagcgcttt ctctcagcct cctcccccc      60 cccatcccct cccccacccg cccgtctcg cgcccgccc gccctcggc ccgcggggtt      120 ccaaggacgg ttggtcgccc ccgccacagt cactcggccg ctcagagcgg cggggcgcac    180
ggggtcgaga gagccagctc tagggtttgg ggctgggaac tga                      223
```

```
<210> SEQ ID NO 8
<211> LENGTH: 134
<212> TYPE: DNA
<213> ORGANISM: human
```

<400> SEQUENCE: 8

```
cccccacccg ccccgtctcg cgcccgcccc gcccctcggc ccgcggggtt ccaaggacgg    60
ttggtcgccc ccgccacagt cactcggccg ctcagagcgg cggggcgcac ggggtcgaga   120
gagccagctc tagg                                                    134

<210> SEQ ID NO 9
<211> LENGTH: 262
<212> TYPE: DNA
<213> ORGANISM: Artificial
<220> FEATURE:
<223> OTHER INFORMATION: bisulfated

<400> SEQUENCE: 9
gttttaagaa tttgggtttt tattttttag gcgttttttt tggaggtttt ttagggatcg    60
tttatagcgt tttttttag tttttttttt ttttttattt tttttttat tcgtttcgtt   120 tcgcgttcgt ttcgttttc ggttcgcggg gttttaagga cggttggtcg ttttcgttat   180
agttattcgg tcgtttagag cggcggggcg tacggggtcg agagagttag ttttagggtt   240 tgggggttggg aattgaagtt tg                                          262

<210> SEQ ID NO 10
<211> LENGTH: 30
<212> TYPE: DNA
<213> ORGANISM: human

<400> SEQUENCE: 10
gttttaagaa tttgggtttt tattttttag                                    30

<210> SEQ ID NO 11
<211> LENGTH: 25
<212> TYPE: DNA
<213> ORGANISM: human

<400> SEQUENCE: 11
caaacttcaa ttcccaaccc caaac                                         25

<210> SEQ ID NO 12
<211> LENGTH: 223
<212> TYPE: DNA
<213> ORGANISM: human

<400> SEQUENCE: 12
ttagttttta gttttaaatt ttagagttgg ttttttcgat tcgtgcgtt tcgtcgtttt    60 gagcggtcga gtgattgtgg cggggggcgat taatcgtttt tggaatttcg cgggtcgagg   120
ggcggggcgg gcgcgagacg gggcggtgg gggaggggat gggggggggg aggaggttga   180
gagaaagcgt tgtgggcggt ttttgaaggg tttttaaggg aga                    223

<210> SEQ ID NO 13
<211> LENGTH: 30
<212> TYPE: DNA
<213> ORGANISM: human

<400> SEQUENCE: 13
ttagttttta gttttaaatt ttagagttgg                                    30

<210> SEQ ID NO 14
<211> LENGTH: 26
<212> TYPE: DNA
<213> ORGANISM: human

<400> SEQUENCE: 14
```

```
tctcccttaa aaaccttca aaaacc                                              26

<210> SEQ ID NO 15
<211> LENGTH: 18
<212> TYPE: DNA
<213> ORGANISM: human

<400> SEQUENCE: 15
taatygtttt tggaattt                                                      18

<210> SEQ ID NO 16
<211> LENGTH: 134
<212> TYPE: DNA
<213> ORGANISM: human

<400> SEQUENCE: 16
tttttattcg tttcgtttcg cgttcgtttc gttttcggt tcgcggggtt ttaaggacgg         60
ttggtcgttt tcgttatagt tattcggtcg tttagagcgg cggggcgtac ggggtcgaga       120
gagttagttt tagg                                                        134

<210> SEQ ID NO 17
<211> LENGTH: 25
<212> TYPE: DNA
<213> ORGANISM: human

<400> SEQUENCE: 17
attcgtttcg tttcgcgttc gtttc                                              25

<210> SEQ ID NO 18
<211> LENGTH: 24
<212> TYPE: DNA
<213> ORGANISM: human

<400> SEQUENCE: 18
ctaaaactaa ctctctcgac cccg                                               24

<210> SEQ ID NO 19
<211> LENGTH: 31
<212> TYPE: DNA
<213> ORGANISM: human

<400> SEQUENCE: 19
tttttatttg ttttgttttg tgtttgtttt g                                       31

<210> SEQ ID NO 20
<211> LENGTH: 25
<212> TYPE: DNA
<213> ORGANISM: human

<400> SEQUENCE: 20
cctaaaacta actctctcaa cccca                                              25

<210> SEQ ID NO 21
<211> LENGTH: 223
<212> TYPE: PRT
<213> ORGANISM: human

<400> SEQUENCE: 21

Met Arg Asp Glu Ile Ala Thr Thr Val Phe Phe Val Thr Arg Leu Val
1               5                   10                  15

Lys Lys His Asp Lys Leu Ser Lys Gln Gln Ile Glu Asp Phe Ala Glu
```

```
              20                  25                  30
Lys Leu Met Thr Ile Leu Phe Glu Thr Tyr Arg Ser His Trp His Ser
             35                  40                  45

Asp Cys Pro Ser Lys Gly Gln Ala Phe Arg Cys Ile Arg Ile Asn Asn
         50                  55                  60

Asn Gln Asn Lys Asp Pro Ile Leu Glu Arg Ala Cys Val Glu Ser Asn
 65                  70                  75                  80

Val Asp Phe Ser His Leu Gly Leu Pro Lys Glu Met Thr Ile Trp Val
                 85                  90                  95

Asp Pro Phe Glu Val Cys Cys Arg Tyr Gly Glu Lys Asn His Pro Phe
            100                 105                 110

Thr Val Ala Ser Phe Lys Gly Arg Trp Glu Glu Trp Glu Leu Tyr Gln
        115                 120                 125

Gln Ile Ser Tyr Ala Val Ser Arg Ala Ser Ser Asp Val Ser Ser Gly
    130                 135                 140

Thr Ser Cys Asp Glu Glu Ser Cys Ser Lys Glu Pro Arg Val Ile Pro
145                 150                 155                 160

Lys Val Ser Asn Pro Lys Ser Ile Tyr Gln Val Glu Asn Leu Lys Gln
                165                 170                 175

Pro Phe Gln Ser Trp Leu Gln Ile Pro Arg Lys Lys Asn Val Val Asp
            180                 185                 190

Gly Arg Val Gly Leu Leu Gly Asn Thr Tyr His Gly Ser Gln Lys His
        195                 200                 205

Pro Lys Cys Tyr Arg Pro Ala Met His Arg Leu Asp Arg Ile Leu
    210                 215                 220

<210> SEQ ID NO 22
<211> LENGTH: 672
<212> TYPE: DNA
<213> ORGANISM: human

<400> SEQUENCE: 22
atgagagatg aaattgcaac aacagttttc tttgtcacaa gattggtgaa aaacatgat       60 aaactaagta acagcaaat agaagacttt gcagaaaagc tgatgacgat cttgtttgaa      120
acatacagaa gtcactggca ctctgattgc ccttctaaag ggcaagcctt caggtgcatc     180
aggataaaca acaatcagaa taaagatccc attctagaaa gggcatgtgt ggaaagtaat    240
gtagattttt ctcacctggg acttccgaag gagatgacca tatgggtaga tcccttgaa     300 gtatgctgta ggtatggtga gaaaaaccat ccatttacag ttgcttcttt taaaggcaga    360
tgggaggaat gggaactata tcaacaaatc agttatgccg ttagtagagc ctcatcagac    420
gtttcctctg gcacttcctg cgatgaagaa agttgtagca aggaacctcg tgtcattcct    480
aaagtcagca atccgaagag tatttatcag gttgaaaact gaaacagcc ctttcaatct    540 tggttacaaa tcccccgcaa aaagaatgtg gtggacggcc gtgttggcct cctgggaaac    600
acttaccatg gctcgcagaa gcatcctaag tgttacaggc ctgctatgca ccggctggac    660 agaatttat aa                                                         672

<210> SEQ ID NO 23
<211> LENGTH: 20
<212> TYPE: DNA
<213> ORGANISM: human

<400> SEQUENCE: 23
aggcatgcct agacatgaac                                                 20
```

```
<210> SEQ ID NO 24
<211> LENGTH: 317
<212> TYPE: DNA
<213> ORGANISM: human

<400> SEQUENCE: 24
ccaacagagc acagaggtgc agatgagact ctccaagcca tcctcccata tgtcagaggc      60
tacccaagcc cacctccatt tggaaaattc aaacctataa tttgaggtac ctgggaagcc     120
gctttcccag ggcggaatgg tcacggaaac tgggtaggct gggggccttc ttggggaatg     180
agggagtgga ggagctcttt gtccctcctg ctagatcaga aagagaaacg tctcaagaat     240
ctgggcctcc atcttctagg cgtctccctt ggaggcccctt cagggaccgc ccacagcgct     300
ttctctcagc ctcctcc                                                    317

<210> SEQ ID NO 25
<211> LENGTH: 413
<212> TYPE: DNA
<213> ORGANISM: human

<400> SEQUENCE: 25
gcacaacacg cgtagctggg ccagcgggcg gcgctgccgg ggaggacccg cgcctccca      60 ggccgggagc cgcgccccga cccccatgac ccccaggagt gccaggcctc cccttcccgc    120
agcctcccgc tcctctcagg gccctcccgc tcaggttccc ctcgcttttc ctttcccctt    180
cgcctcctcg gcccgggctc ccacttcctt cacgccaggc ttcagttccc agccccaaac    240
cctagagctg gtctctcga ccccgtgcgc cccgccgctc tgagcggccg agtgactgtg     300 gcggggcga ccaaccgtcc ttggaacccc gcgggccgag gggcggggcg ggcgcgagac    360
ggggcgggtg ggggagggga tgggggggggg gaggaggctg agagaaagcg ctg         413

<210> SEQ ID NO 26
<211> LENGTH: 24
<212> TYPE: DNA
<213> ORGANISM: human

<400> SEQUENCE: 26
gtttctcttt ctgatctagc agga                                            24

<210> SEQ ID NO 27
<211> LENGTH: 23
<212> TYPE: DNA
<213> ORGANISM: human

<400> SEQUENCE: 27
tcagagtgcc agtgacttct gta                                             23
```